(12) United States Patent
Hu et al.

(10) Patent No.: US 12,297,160 B2
(45) Date of Patent: May 13, 2025

(54) LIQUID-SOLID RADIAL MOVING BED REACTION DEVICE AND SOLID ACID ALKYLATION METHOD

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Lifeng Hu, Beijing (CN); Shuandi Hou, Beijing (CN); Junyi Mao, Beijing (CN); Zhenxing Zhu, Beijing (CN); Xiaojin Tang, Beijing (CN); Zheng Liu, Beijing (CN); Yongxiang Li, Beijing (CN); Zhihai Zhao, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 983 days.

(21) Appl. No.: 17/289,773

(22) PCT Filed: Oct. 29, 2019

(86) PCT No.: PCT/CN2019/113950
§ 371 (c)(1),
(2) Date: Apr. 29, 2021

(87) PCT Pub. No.: WO2020/088440
PCT Pub. Date: May 7, 2020

(65) Prior Publication Data
US 2021/0394143 A1    Dec. 23, 2021

(30) Foreign Application Priority Data

Oct. 29, 2018  (CN) .......................... 201811270073.7
Oct. 29, 2018  (CN) .......................... 201811270089.8

(51) Int. Cl.
C07C 2/58    (2006.01)
B01J 8/08    (2006.01)
(Continued)

(52) U.S. Cl.
CPC ................. *C07C 2/58* (2013.01); *B01J 8/085* (2013.01); *B01J 8/12* (2013.01); *B01J 8/125* (2013.01);
(Continued)

(58) Field of Classification Search
CPC ......... B01J 8/0415; B01J 8/0419; B01J 8/125
See application file for complete search history.

(56) References Cited

U.S. PATENT DOCUMENTS 2,475,855 A * 7/1949 Peters .................... B01J 8/0415
422/636
3,573,200 A * 3/1971 Vogel .................... B01J 8/0015
422/219
(Continued)

FOREIGN PATENT DOCUMENTS

CN    102191081 A    9/2011
CN    105396517 A    3/2016
(Continued)

OTHER PUBLICATIONS

Supplementary European Search Report in counterpart European Patent Application No. EP19879861, mailed Jul. 11, 2022.
(Continued)

*Primary Examiner* — Jennifer A Leung
(74) *Attorney, Agent, or Firm* — FINNEGAN, HENDERSON, FARABOW, GARRETT & GARRETT & DUNNER LLP

(57) ABSTRACT

The present disclosure generally relates to a liquid-solid radial moving bed reaction apparatus comprising a radial moving bed reactor, a spent catalyst receiver, a catalyst
(Continued)

regenerator, and a regenerated catalyst receiver that are successively connected. Also disclosed is a solid acid alkylation process using the liquid-solid radial moving bed reaction apparatus.

28 Claims, 4 Drawing Sheets

(51) Int. Cl.
*B01J 8/12* (2006.01)
*C07C 2/62* (2006.01)
*C10G 29/20* (2006.01)
*B01J 8/04* (2006.01)

(52) U.S. Cl.
CPC .............. *C07C 2/62* (2013.01); *C10G 29/205* (2013.01); *B01J 8/0415* (2013.01); *B01J 2208/00849* (2013.01); *B01J 2208/00902* (2013.01); *B01J 2208/00929* (2013.01); *C10G 2300/4081* (2013.01)

(56) References Cited

U.S. PATENT DOCUMENTS

| | | | | |
|---|---|---|---|---|
| 4,420,418 A * | 12/1983 | Chu | ...................... | C07C 2/66 502/77 |
| 4,446,112 A | 5/1984 | Den Hartog | | |
| 4,879,424 A * | 11/1989 | Harandi | ..................... | B01J 8/12 585/407 |
| 5,840,176 A * | 11/1998 | Lawrence | .............. | C10G 35/10 208/174 |
| 5,849,976 A | 12/1998 | Gosling et al. | | |
| 5,863,419 A | 1/1999 | Huff, Jr. et al. | | |
| 5,879,537 A * | 3/1999 | Peters | .................... | C10G 65/00 208/80 |
| 6,689,331 B1 * | 2/2004 | Brunet | ..................... | B01J 38/24 422/219 |
| 7,582,268 B1 * | 9/2009 | Bozzano | .................. | B01J 8/082 422/216 |
| 8,373,014 B2 | 2/2013 | Sadler et al. | | |
| 2007/0088092 A1 * | 4/2007 | Klanner | .................. | B01J 8/067 518/726 |
| 2011/0152590 A1 | 6/2011 | Sadler et al. | | |

FOREIGN PATENT DOCUMENTS

| | | |
|---|---|---|
| CN | 105441116 A | 3/2016 |
| CN | 105457566 A | 4/2016 |
| CN | 105567306 A | 5/2016 |
| CN | 105617946 A | 6/2016 |
| CN | 107983270 A | 5/2018 |
| CN | 209254707 U | 8/2019 |

OTHER PUBLICATIONS

International Search Report of International Application No. PCT/CN2019/113950, dated Jan. 22, 2020.

* cited by examiner

LIQUID-SOLID RADIAL MOVING BED REACTION DEVICE AND SOLID ACID ALKYLATION METHOD

CROSS-REFERENCE TO RELATED APPLICATIONS

This application is a national stage filing under 35 U.S.C. § 371 of International Application No. PCT/CN2019/113950, filed Oct. 29, 2019, which claims the priority to and benefits of Chinese Patent Application Nos. 201811270089.8 and 201811270073.7, filed Oct. 29, 2018, which are both incorporated herein by reference in their entireties.

TECHNICAL FIELD

The present invention relates to the field of solid acid alkylation. Specifically, the present invention relates to a liquid-solid radial moving bed reaction apparatus, further specifically relates to a liquid-solid radial moving bed reaction apparatus for the solid acid alkylation process. The present invention also relates to a solid acid alkylation process.

BACKGROUND TECHNOLOGY

At present, one of the most important tasks of the oil refining industry is to provide transportation fuel. As an important transportation fuel, gasoline is widely used in communication and transportation, and other industries. With the increase in gasoline consumption and increasingly strict environmental protection standards, how to solve the problem of clean gasoline production has become a hot topic of research and discussion.

Under the action of strong acid, the technology of using isoparaffins (mainly isobutane) and alkenes (C3-C5 olefins) as raw materials to produce an alkylation oil provides the possibility for the clean production of gasoline. The alkylation oil has a high octane number and a low vapor pressure. It is mainly composed of saturated hydrocarbons and does not contain sulfur, nitrogen, alkenes, aromatic hydrocarbons, and the like. Therefore, it is called clean gasoline and is an ideal blending component for aviation gasoline and motor gasoline.

Alkylation technology can be divided into liquid acid alkylation and solid acid alkylation according to the catalyst form.

At present, about 90% of the world's alkylation capacity is provided by the liquid acid alkylation technology (sulfuric acid process and hydrofluoric acid process), although the liquid acid alkylation technology is relatively mature and has better reaction selectivity, however, there are many problems. For example, the liquid acid alkylation process has serious equipment corrosion problems. In addition, for the sulfuric acid process, this process consumes a large amount of the acid, and a large amount of waste acid has certain safety hazards in transportation and disposal. For the hydrofluoric acid process, because hydrofluoric acid has strong causticity and toxicity and is easily volatile, this process can cause great harm to the human body.

Therefore, in contrast, using a solid acid as the catalyst not only does not cause pollution to the environment but also does not have the problem of equipment corrosion. It can be regarded as a green alkylation technology with good development prospects.

However, in the solid acid alkylation process, since the solid acid catalyst is easy to deactivate, to maintain a certain reaction activity, frequent regeneration operations are required. Therefore, the development of reactor technology that can realize the continuous reaction and regeneration is very important to promote the development of solid acid alkylation technology.

U.S. Pat. No. 5,849,976A discloses a solid acid alkylation process using a reactor with a slow axial moving bed reaction zone and a moving bed regeneration zone. In this process, a cooling area where a part of the liquid-phase mixed stream is drawn out for heat-exchanging and then pumped back for the direct mixing and cooling is arranged in a reaction area to take out the reaction heat of the alkylation reaction, and simultaneously, the catalyst can pass through the cooling area before flowing downwards and entering the next bed to realize the cooling of the catalyst; on the other hand, the deactivated catalyst is periodically regenerated with a hydrogen-containing stream to restore the activity of the catalyst.

U.S. Pat. No. 8,373,014 discloses a solid acid alkylation reaction process using the radial moving beds that are overlapped each other as the reactor. In this process, a structure similar to the overlapping radial moving bed for catalytic reforming is adopted. The single-stage reactor is provided with an annular barrel for distributing the reaction streams on the periphery and a central tube for collecting the streams and the reaction bed zone sandwiched between the two; the catalyst stream delivery pipe is used between the two reactors to deliver the catalyst in the upper catalyst bed to the reaction bed zone of the lower reactor. The effluent stream in the intermediate reactor is divided into two parts. One part is pumped back to the upstream reactor and mixed with the fresh feedstock as the feed to the upstream reactor after being mixed with the mixer. This part can be called the recycled stream. The other part is mixed with the fresh feedstock and then introduced into the feed mixer of the downstream reactor as the feed to the downstream reactor, and this part is directly used without pump pressurization. In addition, a part of the recycled stream needs to pass through a heat exchanger to take out the reaction heat.

SUMMARY OF THE INVENTION

The object of the present invention is to provide a liquid-solid radial moving bed reaction apparatus and a solid acid alkylation process using the liquid-solid radial moving bed reaction apparatus.

Specifically, the present invention provides the following technical solutions:

1. A liquid-solid radial moving bed reaction apparatus, which is characterized in that the apparatus comprises:

A radial moving bed reactor, a spent catalyst receiver, a catalyst regenerator, and a regenerated catalyst receiver that are successively connected, wherein the catalyst discharging outlet of the regenerated catalyst receiver is communicated with the catalyst inlet of the radial moving bed reactor; a reaction stream distribution zone, a catalyst bed, and a stream-after-the-reaction collection zone are arranged in the radial moving bed reactor from the inside to the outside or from the outside to the inside, the reaction stream distribution zone is communicated with the reaction stream feeding pipeline; the stream-after-the-reaction collection zone is communicated with the stream-after-the-reaction withdrawing pipe;

A component-based mixer is arranged on the reaction stream feeding pipeline; the component-based mixer consists of an upper recycled stream pipe, a lower reaction stream feeding pipe, and a fresh feedstock feeding pipe extending into the reaction stream feeding pipeline, a nozzle of the feeding pipe is arranged at the outlet of the fresh feedstock feeding pipe, a filler and/or a mixing fin is arranged in the reaction stream feeding pipeline, wherein the component-based mixer is located out of the radial moving bed reactor.

2. The liquid-solid radial moving bed reaction apparatus according to technical solution 1, which is characterized in that the radial moving bed reactor is provided with at least two reaction beds, a catalyst delivery pipe is arranged between two adjacent reaction beds so that the catalyst can move in the radial moving bed reactor from top to bottom; a reaction stream space is arranged between two reaction beds, the reaction stream distribution zone is communicated through the reaction stream space with the reaction stream feeding pipeline; the component-based mixer is arranged on the reaction stream feeding pipeline of each reaction bed.

3. The liquid-solid radial moving bed reaction apparatus according to any of technical solutions 1-2, which is characterized in that an L-shaped or approximately L-shaped stream delivery valve manifold is arranged on the pipeline between the catalyst discharging outlet at the bottom of the radial moving bed reactor and the spent catalyst receiver, the discharge rate of the catalyst is regulated by changing the flow of the liquid-phase mixed stream into the valve manifold.

4. The liquid-solid radial moving bed reaction apparatus according to any of technical solutions 1-3, which is characterized in that a top catalyst collection zone is arranged at the top of the radial moving bed reactor, the catalyst inlet is communicated through the top catalyst collection zone with the catalyst delivery pipe.

5. The liquid-solid radial moving bed reaction apparatus according to any of technical solutions 1-4, which is characterized in that in the radial moving bed reactor, the recycled stream pipe of the component-based mixer of the next reaction bed is the stream-after-the-reaction withdrawing pipe of the previous reaction bed (or, is communicated with the stream-after-the-reaction withdrawing pipe of the previous reaction bed), the recycled stream pipe of the component-based mixer of the first reaction bed is communicated with the stream-after-the-reaction withdrawing pipe of the last reaction bed.

6. The liquid-solid radial moving bed reaction apparatus according to any of technical solutions 1-5, which is characterized in that catalyst circulation pipelines for connecting the spent catalyst receiver, the catalyst regenerator, and the regenerated catalyst receiver are arranged vertically or inclined at an angle relative to the horizontal plane of not less than 40 degrees.

7. The liquid-solid radial moving bed reaction apparatus according to any of technical solutions 1-6, which is characterized in that the catalyst regenerator or the regenerated catalyst receiver is further provided with a fresh catalyst charging inlet.

8. The liquid-solid radial moving bed reaction apparatus according to any of technical solutions 1-7, which is characterized in that a regeneration medium inlet is arranged at the upper part of the catalyst regenerator, a regeneration medium outlet is arranged at the bottom of or the bottom discharging pipeline of the catalyst regenerator; the regeneration medium inlet is positioned at 70% or higher of the straight-tube segment of the catalyst regenerator from bottom to top, the regeneration medium outlet is positioned at 20% or lower of the straight-tube segment of the catalyst regenerator from bottom to top.

9. The liquid-solid radial moving bed reaction apparatus according to any of technical solutions 1-8, which is characterized in that the pipeline starting from the regeneration medium outlet of the catalyst regenerator is further provided with a filter.

10. The liquid-solid radial moving bed reaction apparatus according to any of technical solutions 1-9, which is characterized in that a liquid-phase mixed stream discharging outlet is arranged at the bottom of or the bottom discharging pipeline of the spent catalyst receiver.

11. The liquid-solid radial moving bed reaction apparatus according to any of technical solutions 1-10, which is characterized in that in the component-based mixer, the ratio of the cross-sectional area of the fresh feedstock feeding pipe to the cross-sectional area of the recycled stream pipe is 0.001-0.5:1, preferably 0.002-0.1:1.

12. The liquid-solid radial moving bed reaction apparatus according to any of technical solutions 1-11, which is characterized in that at least one reaction bed and at least one regeneration bed are arranged up and down in the radial moving bed reactor, preferably, the number of the reaction bed(s) is 2-8, for example, 4-8, the number of the regeneration bed(s) is 2-8, for example, 4-8, preferably 2-7, for example, 4-7; more preferably, the number of the regeneration bed(s) and the number of the reaction bed(s) are identical and one regeneration bed is arranged immediately below each reaction bed, or more preferably, the number of the regeneration bed is less than the number of the reaction bed by one, the reaction bed and the regeneration bed are intervally successively arranged, and the reaction beds are arranged both at the top and the bottom of the radial moving bed reactor;

Each reaction bed comprises a reaction stream distribution zone, a catalyst bed, and a stream-after-the-reaction collection zone, and each reaction bed has a reaction stream feeding pipeline and a stream-after-the-reaction withdrawing pipe, the reaction stream distribution zone is communicated through the reaction stream space with the reaction stream feeding pipeline, the stream-after-the-reaction collection zone is communicated with the stream-after-the-reaction withdrawing pipe, the component-based mixer is arranged on the reaction stream feeding pipeline of each reaction bed; Each regeneration bed correspondingly comprises a regeneration medium distribution zone, a catalyst bed, and a regeneration medium collection zone, and each regeneration bed has a regeneration medium feeding pipe and a regeneration medium withdrawing pipe, the regeneration medium distribution zone is communicated (via the regeneration medium space) with the regeneration medium feeding pipe, the regeneration medium collection zone is communicated with the regeneration medium withdrawing pipe; Any two adjacent beds of the reaction bed(s) and the regeneration bed(s) are communicated through the catalyst delivery pipe so that the catalyst can move in the radial moving bed reactor from top to bottom; the catalyst in the reaction bed and the catalyst in the regeneration bed fall through the catalyst delivery pipe from the upstream bed to the adjacent downstream bed, finally, fall to the bottom catalyst-collecting area, and leave the radial moving bed reactor;

Preferably, the regeneration medium feeding pipe of any regeneration bed except the first regeneration bed can be or be communicated with the regeneration medium withdrawing pipe of the previous regeneration bed (upstream bed).

13. A solid acid alkylation process, which is characterized in that the liquid-solid radial moving bed reaction apparatus according to any of technical solutions 1-12 is used, an alkylation raw material and a recycled stream are mixed with the component-based mixer and enter the radial moving bed reactor in one or more sections; the liquid-phase mixed stream, after the distribution with the reaction stream distribution zone, passes through the catalyst bed along the radial direction, contacts with the solid acid catalyst to perform the reaction, and the liquid-phase mixed stream-after-the-reaction reaches the stream collection zone, and is used as the recycled stream or further separated to produce the alkylation oil product; the solid acid catalyst in the catalyst bed of the radial moving bed reactor gradually deactivates, falls bed by bed, finally falls to the bottom catalyst-collecting area, leaves the radial moving bed reactor, enters the spent catalyst receiver, in which the liquid-phase mixed stream carried in the catalyst is removed, subsequently flows into the catalyst regenerator to perform the regeneration reaction, the regenerated catalyst with recovered activity flows into the regenerated catalyst receiver, in which the gas therein is replaced and removed, and returns to the radial moving bed reactor for continuous reaction.

14. The solid acid alkylation process according to technical solution 13, which is characterized in that the alkylation raw material is a hydrocarbon fraction containing alkenes and alkanes.

15. The solid acid alkylation process according to any of technical solutions 13-14, which is characterized in that in the radial moving bed reactor, the reaction temperature is 30-100° C., the superficial flow velocity of the liquid-phase mixed stream in the reactor is 0.05-1 m/s; the weight hourly space velocity of the mixed alkene feedstock is 0.05-1 $h^{-1}$; the mole ratio of alkane to alkene at the inlet of the reaction bed is 200-1000:1; the average particle diameter of the solid acid catalyst particles is 0.3-3 mm 16. The solid acid alkylation process according to any of technical solutions 13-15, which is characterized in that the catalyst is a solid acid catalyst, containing 95 wt %-65 wt % of a molecular sieve and 5 wt %-35 wt % of a heat-resistant inorganic oxide, wherein the molecular sieve is selected from one or more of FAU structure zeolite, BETA structure zeolite, and MFI structure zeolite, the heat-resistant inorganic oxide is alumina and/or silica.

17. The solid acid alkylation process according to any of technical solutions 13-15, which is characterized in that in the catalyst regenerator, the spent catalyst and an oxygen-containing gas are subjected to the oxidizing reaction under the conditions of the temperature being 200-500° C. and the pressure being 0.01-0.5 MPa, the carbon deposited on the spent catalyst is removed to recover the activity of the catalyst.

18. The solid acid alkylation process according to any of technical solutions 13-15, which is characterized in that in the catalyst regenerator, the spent catalyst is contacted with a hydrogen gas-containing regeneration medium to perform the reaction, the carbon deposited on the spent catalyst is removed to recover the activity of the catalyst, the regeneration temperature is 100-400° C., the regeneration pressure is 0.5-3.5 MPa.

19. The solid acid alkylation process according to any of technical solution 17 or 18, which is characterized in that the liquid-solid radial moving bed reaction apparatus according to technical solution 12 is used, wherein:

The fresh feedstock and the recycled stream or the stream-after-the-reaction from the upstream reactor are mixed and then sent into the reaction bed of the radial moving bed reactor;

In the reaction bed of the reactor, the mixed stream passes through the reaction bed along the radial direction of the reactor, and contacts with the solid acid catalyst to perform the reaction, after the completion of the reaction, the majority of (for example, >50 vol %, >60 vol %, >70 vol %, >80 vol %, >90 vol %, >95 vol %, >96 vol %, >97 vol %, >98 vol %, or >99 vol %) liquid-phase mixed stream is discharged off this bed through the arranged reaction product discharging outlet, while the minority of the remaining liquid-phase mixed stream, together with the catalyst particles, enters the next reaction bed through the catalyst delivery pipe or enters the catalyst regeneration bed through the catalyst delivery pipe between the reaction bed and the catalyst regeneration bed;

The discharged liquid-phase mixed stream-after-the-reaction, is mixed with the fresh feedstock and then sent into the downstream reaction bed of the reactor to continue to participate in the reaction, or is discharged off the reactor, an alkylation oil product is collected by separation (for example distillation);

In the catalyst regeneration bed, the regenerating medium enters the catalyst regeneration bed of the radial moving bed reactor through the regenerating medium space and the regenerating medium distribution zone, the unsaturated hydrocarbons adsorbed on the catalyst are converted with the catalyst by contacting with the liquid-phase regeneration medium in which hydrogen is dissolved under the low-temperature regeneration condition to the saturated hydrocarbon molecules that are easily desorbed, and the saturated hydrocarbon molecules are taken out of the regenerator to realize the partial regeneration of the catalyst;

The regeneration medium can optionally enter the next catalyst regeneration bed via the pipeline to perform the low-temperature regeneration;

The low-temperature regenerated catalyst flows into the next reaction bed through the catalyst delivery pipe at the bottom of the catalyst regeneration bed;

The inactivation degree of the catalyst in every reaction beds and every catalyst regeneration beds of the radial moving bed reactor will gradually increase along with the reaction and the increased regeneration number, and meanwhile, the catalyst will also gradually fall to the lower reaction bed or the lower catalyst regeneration bed, and finally reach the catalyst discharging outlet at the bottom of the radial moving bed reactor; finally, the catalyst is sent to the catalyst regenerator to perform the high-temperature deep regeneration to realize the complete recovery of the catalyst activity;

The catalyst with the recovered activity is sent to the catalyst inlet at the top of the radial moving bed reactor to continue to participate in the reaction;

In the radial moving bed reactor, in the reaction bed, the reaction temperature is 30-100° C., the reaction pressure is 1.0-5.0 MPa, the superficial flow velocity of the liquid-phase mixed stream in the reactor is 0.03-1 m/s; the weight hourly space velocity of the mixed alkene feedstock is 0.05-1 $h^{-1}$; the mole ratio of alkane to alkene at the reaction bed inlet is 200-1000:1; the average particle diameter of the solid acid catalyst particles is 0.3-3 mm; In the catalyst regeneration bed, the regeneration temperature is 50-140° C., the superficial flow velocity of the regeneration medium in the regeneration bed is 0.01-0.5 m/s; the regeneration medium is a liquid hydrocarbon in which hydrogen is dissolved; the liquid hydrocarbon is C3-C5 saturated alkane or a mixture of the reaction product and the above-mentioned saturated alkane, preferably, the liquid hydrocarbon is a mixture of C3-C5 saturated alkane and the reaction product;

The main active component of the catalyst is a molecular sieve loaded with a certain amount of metal, said molecular sieve is one of or a combination of two or more of FAU structure zeolite, BETA structure zeolite, and MFI structure zeolite, preferably a zeolite having FAU structure and a zeolite having BETA structure; the metal loaded on the catalyst is one of or a combination of two or more of Fe, Co, Ni, Pd and/or Pt, preferably one of or a combination of two or more of Co, Ni or Pt, more preferably Pt;

In the catalyst regenerator, the regeneration temperature is 180-400° C., the regeneration pressure is 0.5-4.0 MPa, the regeneration medium is hydrogen gas or a mixture of hydrogen gas and low carbon hydrocarbon (for example C3-C8), preferably a mixture of hydrogen gas and low carbon hydrocarbon (for example C3-C8).

The beneficial effects of the present invention are as follows:

The liquid-solid radial moving bed reaction apparatus provided by the present invention has the advantages of simple structure and flexible assembly and is suitable for solid acid alkylation reaction. The fresh alkylation stream and the recycled stream are mixed uniformly in a component-based mixer outside the radial moving bed reactor and introduced through a reaction stream feeding pipeline for reaction. For the catalyst stream, the radial moving bed reactor, the spent catalyst receiver, the catalyst regenerator, the regenerated catalyst receiver, and the catalyst collection zone at the top of the radial moving bed reactor are communicated with each other, which ensures the continuous flow of the solid acid catalyst particles in the radial moving bed reactor, and the alkylation reaction and the solid acid catalyst regeneration can be performed simultaneously without mutual interference. The alkylation stream can be uniformly mixed, the space in the reactor is saved, the reaction efficiency is improved, and the selectivity of the target product is improved.

By applying the solid acid alkylation reaction apparatus provided by the present invention to the solid acid alkylation process, the continuous and stable operation of the alkylation reaction and the deactivated catalyst regeneration can be realized, the selectivity of the target product and the flexibility of the apparatus operation are improved, the equipment investment cost is reduced, and the economic competitiveness of the apparatus is increased.

DESCRIPTION OF THE REFERENCE NUMERALS

Figure 1:
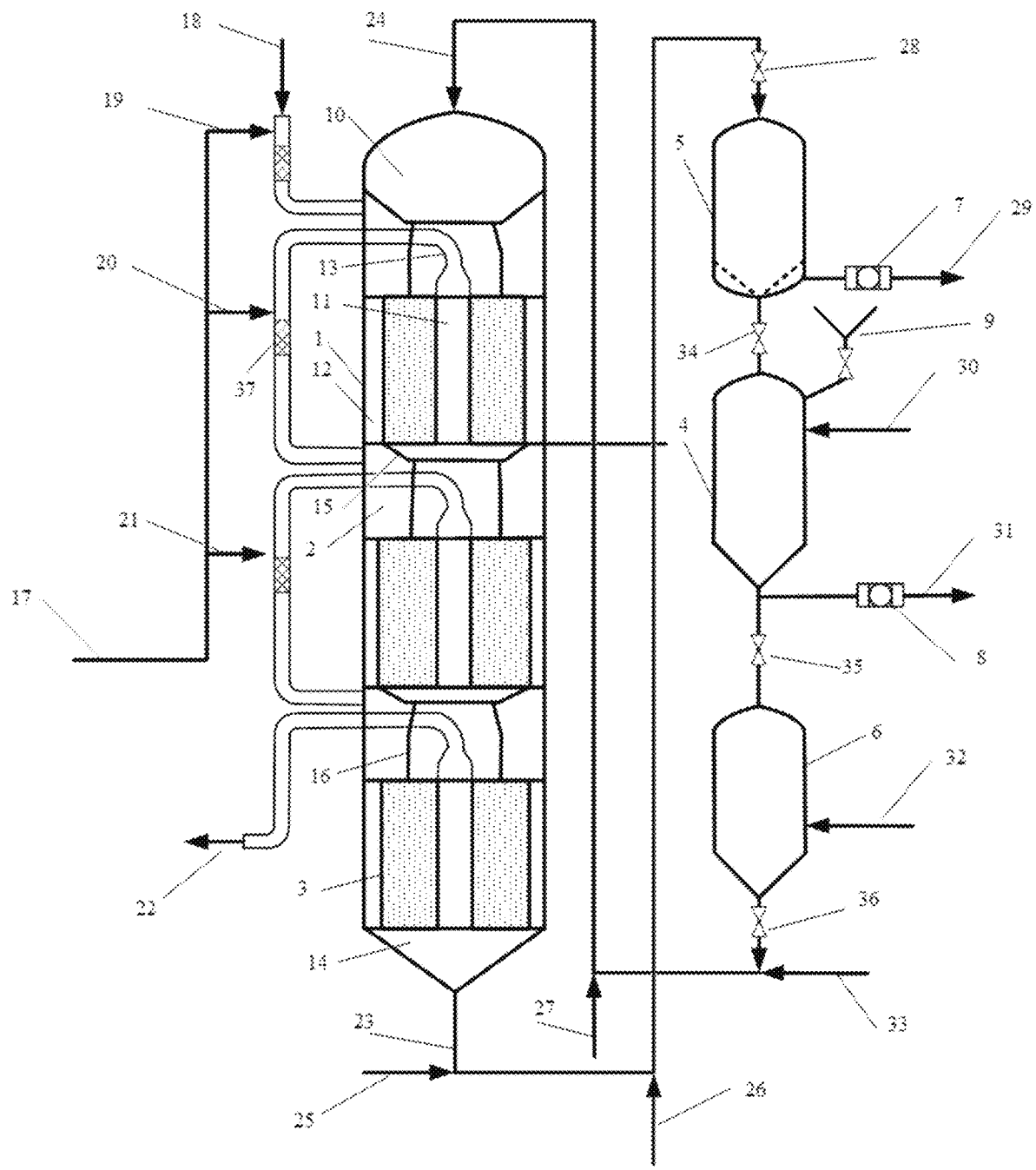
FIG. 1 is a schematic diagram of an embodiment of the radial moving bed reaction apparatus provided by the present invention.

1 Radial moving bed reactor;
2 Reaction stream space;
3 Catalyst bed;
4 Catalyst regenerator;
5 Spent catalyst receiver;
6 Regenerated catalyst receiver;
7 Removed liquid filter;
8 Medium-after-regeneration filter;
9 Fresh catalyst charging inlet;
10 Top catalyst collection zone;
11 Stream-after-the-reaction collection zone;
12 Reaction stream distribution zone;
13 Stream-after-the-reaction withdrawing pipe;
14 Bottom catalyst-collecting area;
15 Catalyst bed bottom distribution zone;
16 Catalyst delivery pipe;
17 Fresh feedstock feeding pipe;
18 Recycled stream pipe;
19 First branch pipeline;
20 Second branch pipeline;
21 Third branch pipeline;
22 Liquid-phase product outlet;
23 Catalyst discharging outlet;
24 Catalyst inlet;
25, 33 Catalyst particles regulating liquor pipelines;
26, 27 Catalyst particles lifting liquor pipelines;
28, 34, Between-vessels stream pipeline valves;
35, 36
29 Liquid-phase mixed stream discharging outlet;
30 Regeneration medium inlet;
31 Pipeline starting from the regeneration medium outlet/regeneration medium outlet;
32 Liquid-phase mixed stream charging inlet;
37 Component-based mixer;
38 Spent catalyst buffer tank;
51, 53 Reaction beds;
52, 54 Regeneration beds;
61 Stream-after-the-reaction;
62 Fresh regeneration medium;
63 Pipeline;
64 Regeneration medium feeding pipe;
65 Liquid-phase product outlet;
91 Recycled stream pipe;
92 Feeding pipe;
93 Fresh feedstock feeding pipe;
94 Nozzle of the feeding pipe;
95 Mixing fin.

DETAILED DESCRIPTION OF THE INVENTION

The specific embodiments of the liquid-solid moving bed reaction apparatus provided by the present invention will be described in detail below with reference to the accompanying drawings.

In the first aspect, the present invention provides a liquid-solid radial moving bed reaction apparatus, wherein the apparatus comprises: A radial moving bed reactor, a spent catalyst receiver, a catalyst regenerator, and a regenerated catalyst receiver that are successively connected, wherein the catalyst discharging outlet of the regenerated catalyst receiver is communicated with the catalyst inlet of the radial moving bed reactor; a reaction stream distribution zone, a catalyst bed, and a stream-after-the-reaction collection zone are arranged in the radial moving bed reactor from the inside to the outside or from the outside to the inside, the reaction stream distribution zone is communicated with the reaction stream feeding pipeline; the stream-after-the-reaction collection zone is communicated with the stream-after-the-reaction withdrawing pipe;

A component-based mixer is arranged on the reaction stream feeding pipeline; the component-based mixer consists of an upper recycled stream pipe, a lower reaction stream feeding pipe, and a fresh feedstock feeding pipe extending into the reaction stream feeding pipeline, a nozzle of the feeding pipe is arranged at the outlet of the fresh feedstock feeding pipe, a filler and/or a mixing fin is arranged in the reaction stream feeding pipeline, wherein the component-based mixer is located out of the radial moving bed reactor.

For the component-based mixer arranged on the reaction stream feeding pipeline, the upstream recycled stream pipe and the downstream reaction stream feeding pipe are composed of one pipe or composed of the identical or different pipes, preferably composed by connecting identical pipes; the nozzle of the feeding pipe arranged at the outlet of the fresh feedstock feeding pipe has an upward opening direction with an angle inclined relative to the axis direction of the pipeline of no greater than 60 degrees, 50 degrees, 40 degrees, 30 degrees, 20 degrees, 10 degrees, 5 degrees or 0 degrees; the filler and/or the mixing fin are preferably arranged in the downstream reaction stream feeding pipe.

In an embodiment according to the liquid-solid radial moving bed reaction apparatus of the present invention, the radial moving bed reactor is provided with at least two reaction beds arranged up and down, a catalyst delivery pipe is arranged between two adjacent reaction beds, so that the catalyst can move in the radial moving bed reactor from top to bottom; a reaction stream space is further arranged between two reaction beds, the reaction stream distribution zone is communicated through the reaction stream space with the reaction stream feeding pipeline; the component-based mixer is arranged on the reaction stream feeding pipeline of each reaction bed.

In an embodiment according to the liquid-solid radial moving bed reaction apparatus of the present invention, at least one reaction bed and at least one regeneration bed are arranged up and down in the radial moving bed reactor, so that the catalyst can move in the radial moving bed reactor from top to bottom, preferably, the number of the reaction bed(s) is 2-8, for example, 4-8, the number of the regeneration bed(s) is 2-8, for example, 4-8, preferably 2-7, for example, 4-7; more preferably, the number of the regeneration bed(s) and the number of the reaction bed(s) are identical and one regeneration bed is arranged immediately below each reaction bed, or more preferably, the number of the regeneration bed is less than the number of the reaction bed by one, the reaction bed and the regeneration bed are intervally successively arranged, and the reaction beds are arranged both at the top and the bottom of the radial moving bed reactor;

Each reaction bed comprises a reaction stream distribution zone, a catalyst bed, and a stream-after-the-reaction collection zone, and each reaction bed has a reaction stream feeding pipeline and a stream-after-the-reaction withdrawing pipe, the reaction stream distribution zone is communicated through the reaction stream space with the reaction stream feeding pipeline, the stream-after-the-reaction collection zone is communicated with the stream-after-the-reaction withdrawing pipe, the component-based mixer is arranged on the reaction stream feeding pipeline of each reaction bed;

The regeneration bed has a similar physical structure to the reaction bed, namely, each regeneration bed correspondingly comprises a regeneration medium distribution zone, a catalyst bed, and a regeneration medium collection zone, and each regeneration bed has a regeneration medium feeding pipe and a regeneration medium withdrawing pipe, the regeneration medium distribution zone is communicated via the regeneration medium space with the regeneration medium feeding pipe, the regeneration medium collection zone is communicated with the regeneration medium withdrawing pipe;

Any two adjacent beds of the reaction bed(s) and the regeneration bed(s) are communicated through the catalyst delivery pipe; the catalyst in the reaction bed and the catalyst in the regeneration bed fall through the catalyst delivery pipe from the upstream bed to the adjacent downstream bed, finally, fall to the bottom catalyst-collecting area, and leave the radial moving bed reactor; Preferably, the regeneration medium feeding pipe of any regeneration bed except the first regeneration bed can be the regeneration medium withdrawing pipe of the previous regeneration bed (upstream bed) or can be communicated with the regeneration medium withdrawing pipe of the previous regeneration bed (upstream bed).

In an embodiment, an L-shaped or approximately L-shaped stream delivery valve manifold is arranged on the pipeline between the catalyst discharging outlet at the bottom of the radial moving bed reactor and the spent catalyst receiver, the discharge rate of the catalyst is regulated by changing the flow of the liquid-phase mixed stream into the valve manifold. Compared with the delivery tank, the L-type delivery valve manifold occupies a small area and has a larger adjustment range, and therefore is advantageous. The L-shaped or approximately L-shaped stream delivery valve manifold is the equipment commercially available. The L-shaped or approximately L-shaped stream delivery valve manifold is further communicated with at least one liquid-phase mixed stream feeding pipeline. Arranging the particle flow regulator can increase the flow resistance of the particle stream. At the same time, the regulator is communicated with at least one liquid-phase mixed stream feeding pipeline to increase the flow driving force of the particle stream and reduce the flow resistance of the particle stream. By arranging the L-shaped or approximately L-shaped stream delivery valve manifold and by changing the flow of the liquid-phase mixed stream into the valve manifold, the discharge rate of the catalyst can be adjusted, so that the falling rate and the residence time in each reaction bed of the catalyst in the reactor can be controlled and adjusted.

In an embodiment according to the liquid-solid radial moving bed reaction apparatus of the present invention, the catalyst delivery pipes are respectively arranged between two adjacent beds, between the top catalyst collection zone and the first bed, and between the last bed and the bottom catalyst-collecting area.

In an embodiment according to the liquid-solid radial moving bed reaction apparatus of the present invention, in the radial moving bed reactor, the recycled stream pipe of the component-based mixer of the next reaction bed is the stream-after-the-reaction withdrawing pipe of the previous reaction bed or is communicated with the stream-after-the-reaction withdrawing pipe of the previous reaction bed.

In an embodiment according to the liquid-solid radial moving bed reaction apparatus of the present invention, catalyst circulation pipelines for connecting the spent catalyst receiver, the catalyst regenerator, and the regenerated catalyst receiver are arranged vertically or inclined at an angle relative to the horizontal plane of not less than 40 degrees.

In an embodiment according to the liquid-solid radial moving bed reaction apparatus of the present invention, the catalyst regenerator or the regenerated catalyst receiver is further provided with a fresh catalyst charging inlet.

In an embodiment according to the liquid-solid radial moving bed reaction apparatus of the present invention, a regeneration medium inlet is arranged at the upper part of the catalyst regenerator, a regeneration medium outlet is arranged at the bottom of or the bottom discharging pipeline of the catalyst regenerator; the regeneration medium inlet is positioned at 70% or higher of the straight-tube segment of the catalyst regenerator from bottom to top, the regeneration medium outlet is positioned at 20% or lower of the straight-tube segment of the catalyst regenerator from bottom to top.

In an embodiment according to the liquid-solid radial moving bed reaction apparatus of the present invention, the pipeline starting from the regeneration medium outlet of the catalyst regenerator is further provided with a filter.

In an embodiment according to the liquid-solid radial moving bed reaction apparatus of the present invention, a liquid-phase mixed stream discharging outlet is arranged at the bottom of or the bottom discharging pipeline of the spent catalyst receiver.

In an embodiment according to the liquid-solid radial moving bed reaction apparatus of the present invention, in the component-based mixer, the ratio of the cross-sectional area of the fresh feedstock feeding pipe to the cross-sectional area of the recycled stream pipe is 0.001-0.5:1, more preferably 0.002-0.1:1.

In an embodiment according to the liquid-solid radial moving bed reaction apparatus of the present invention, in the radial moving bed reactor, at least two reaction beds are vertically arranged up and down, preferably, the radial moving bed reactor contains 4-8 reaction beds. Every reaction beds, from the inside to the outside, or from the outside to the inside, all contain a reaction stream feeding pipeline, a reaction stream distribution zone, a (ring-column shaped) catalyst bed, a stream-after-the-reaction collection zone, and a stream-after-the-reaction withdrawing pipe for withdrawing the stream-after-the-reaction. A top catalyst collection zone is arranged at the top of the radial moving bed reactor, and catalyst delivery pipes are arranged between the top catalyst collection zone and the first catalyst bed, between the upstream and downstream catalyst beds, and between the last catalyst bed and the bottom catalyst-collecting area. The catalyst inlet is communicated with the top catalyst collection zone and the catalyst delivery pipe, and the catalyst delivery pipe at the reactor bottom is communicated with the bottom catalyst-collecting area and the catalyst discharging outlet.

In an embodiment according to the liquid-solid radial moving bed reaction apparatus of the present invention, an L-shaped or approximately L-shaped stream delivery valve manifold is arranged on the pipeline between the catalyst discharging outlet and the spent catalyst receiver, and the discharge rate of the catalyst is regulated by changing the flow of the liquid-phase mixed stream into the valve manifold. Thereby the falling rate and the residence time in each reaction bed of the catalyst in the reactor can be controlled and adjusted.

In an embodiment according to the liquid-solid radial moving bed reaction apparatus of the present invention, the component-based mixer can be arranged on the pipeline between the stream-after-the-reaction withdrawing pipe of the previous reaction bed and the reaction stream feeding pipe of the next reaction bed, and the fresh feedstock feeding pipe is used as a supplemental fresh feedstock inlet.

In an embodiment according to the liquid-solid radial moving bed reaction apparatus of the present invention, a spent catalyst buffer tank is arranged below/after the radial moving bed reactor to preserve the spent catalyst discharged from the reactor during the periods of withdrawing the liquid-phase mixed stream from the spent catalyst receiver and discharging the catalyst to the catalyst regenerator, ensuring the catalyst stream flow continuity in the radial moving bed reactor and the smoothness of the apparatus operation.

In an embodiment according to the liquid-solid radial moving bed reaction apparatus of the present invention, the spent catalyst receiver, the catalyst regenerator, and the regenerated catalyst receiver are successively arranged from top to bottom, catalyst circulation pipelines for connecting the spent catalyst receiver, the catalyst regenerator, and the regenerated catalyst receiver are arranged vertically or inclined at an angle relative to the horizontal plane of not less than 40 degrees, which is convenient for the smooth flow of the catalyst particle stream from top to bottom, and prevents the stream from accumulating or remaining in the pipeline, which affects the valve sealing performance or the catalyst regeneration effect.

In an embodiment according to the liquid-solid radial moving bed reaction apparatus of the present invention, the catalyst regenerator is provided with a fresh catalyst charging inlet. By providing the catalyst regenerator with the fresh catalyst charging inlet, a part of the catalyst that has lost its activity or the catalyst that is difficult to restore the initial activity can be replaced with a fresh catalyst to ensure the processing capacity of the apparatus.

In an embodiment according to the liquid-solid radial moving bed reaction apparatus of the present invention, in the liquid-solid radial moving bed reaction apparatus provided by the present invention, a regeneration medium inlet is arranged at the upper part of the catalyst regenerator, and a regeneration medium outlet is arranged at the bottom of or the bottom discharging pipeline of the catalyst regenerator, to introduce and discharge the regeneration medium when the regeneration is performed in the presence of hydrogen gas; the regeneration medium inlet is positioned at 70% or higher of the straight-tube segment of the catalyst regenerator from bottom to top, the regeneration medium outlet is positioned at 20% or lower of the straight-tube segment of the catalyst regenerator from bottom to top, preferably, arranged on the bottom discharging pipeline. Further preferably, the pipeline starting from the regeneration medium outlet of the catalyst regenerator is further provided with a filter. The filter is used to block the catalyst of the regenerator from flowing into the downstream gas circulation pressurizing equipment and to collect the fine powder or fine particles generated during the regeneration process due to friction or purging.

In an embodiment according to the liquid-solid radial moving bed reaction apparatus of the present invention, a liquid-phase mixed stream discharging outlet is arranged at the bottom of or the bottom discharging pipeline of the spent catalyst receiver; the regenerated catalyst receiver or the pipeline introduced into the regenerated catalyst receiver is provided with a liquid-phase mixed stream charging inlet.

Through the liquid-phase mixed stream discharging outlet and the liquid-phase mixed stream charging inlet, the liquid-phase mixed stream carried in the catalyst is evacuated or the liquid-phase mixed stream is added to the regenerated catalyst.

In an embodiment according to the liquid-solid radial moving bed reaction apparatus of the present invention, in the component-based mixer, the ratio of the cross-sectional area of the fresh feedstock feeding pipe to the cross-sectional area of the recycled stream pipe is 0.001-0.5:1, preferably, 0.002-0.1:1. The filler and/or the mixing fin for intensifying the mixing of the stream is arranged in the main feeding pipe of the component-based mixer (namely the upper recycled stream pipe and the lower reaction stream feeding pipe), preferably, arranged in the lower reaction stream feeding pipe. The filler is selected from regular filler or random filler, the mixing fin is selected from the flow guide plate or the fin, preferably a group of inclined fins is arranged.

The liquid-solid radial moving bed reaction apparatus provided by the present invention is suitable for the solid acid alkylation reaction and regeneration process, any of the above liquid-solid radial moving bed reaction apparatus is used, an alkylation raw material and a recycled stream are mixed with the component-based mixer and enter the radial moving bed reactor in one or more sections; the liquid-phase mixed stream, after the distribution with the reaction stream distribution zone, passes through the catalyst bed along the radial direction, contacts with the solid acid catalyst to perform the reaction, and the liquid-phase mixed stream-after-the-reaction reaches the stream collection zone, and is discharged through the stream-after-the-reaction withdrawing pipe, and used as the recycled stream or further separated to produce the alkylation oil product (the discharged stream-after-the-reaction, is mixed with the fresh feedstock by the component-based mixer, and then sent into the next reaction bed to continue to participate in the reaction, or is discharged off the reactor, an alkylation oil product is obtained by separation); the solid acid catalyst in the catalyst bed gradually deactivates, falls bed by bed, finally falls to the bottom catalyst-collecting area, and leaves the radial moving bed reactor; then enters the spent catalyst receiver, in which the liquid-phase mixed stream carried in the catalyst is removed, via the catalyst delivery pipeline, subsequently flows into the catalyst regenerator to perform the regeneration reaction, is regenerated in an oxygen atmosphere or in the presence of hydrogen gas to recover the activity; the regenerated catalyst with recovered activity at the bottom of the catalyst regenerator flows into the regenerated catalyst receiver, and the liquid-phase mixed stream is introduced thereto to replace and remove the gas in the gap of the regenerated catalyst, and then the regenerated catalyst returns to the radial moving bed reactor via the catalyst delivery conduit for the continuous reaction.

The alkylation raw material is a hydrocarbon fraction containing alkene and alkane, preferably C4 fraction containing C4 alkene and C4 alkane, more preferably a mixture of C4 alkene and C4 alkane. In one embodiment, the alkane fraction further comprises a light hydrocarbon fraction that passes through the top of the fractionation column, is cooled, and returns to the reactor inlet. In an embodiment, the alkylation raw material is a hydrocarbon fraction containing alkene and alkane, wherein the mole ratio of alkane to alkene is 5-50:1, for example, 10-40:1 or 20-30:1. In an embodiment, the alkylation raw material is a hydrocarbon fraction containing C3-C5 alkene and C3-C5 alkane, wherein the mole ratio of alkane to alkene is 5-50:1, for example, 10-40:1 or 20-30:1. In an embodiment, the alkylation raw material is a mixture of C3-C5 alkene and C3-C5 alkane, wherein the mole ratio of alkane to alkene is 5-50:1, for example, 10-40:1 or 20-30:1.

In the radial moving bed reactor, the reaction temperature is 30-100° C., the superficial flow velocity of the liquid-phase mixed stream in the reactor is 0.05-1 m/s; the weight hourly space velocity of the mixed alkene feedstock is 0.05-1 $h^{-1}$; the mole ratio of alkane to alkene at the inlet of the reaction bed is 200-1000:1; the average particle diameter of the solid acid catalyst particles is 0.3-3 mm.

The catalyst is a solid acid catalyst, the solid acid catalyst contains a molecular sieve and a heat-resistant inorganic oxide, based on the total amount of the solid acid catalyst, the content of the molecular sieve is 65-95 wt %, the content of the heat-resistant inorganic oxide is 5-35 wt %; preferably, the molecular sieve is selected from at least one of FAU structure zeolite, BETA structure zeolite, and MFI structure zeolite, the heat-resistant inorganic oxide is alumina and/or silica; Further preferably, the solid acid catalyst also contains a metal active component, the metal active component is selected from at least one of Fe, Co, Ni, Pd, and Pt, based on the total amount of the solid acid catalyst, the content of the metal active component is 0.15-2 wt %.

The stream-after-the-reaction withdrawing pipe of the last reaction bed of the radial moving bed reactor is used as the liquid-phase product outlet, the majority of (for example, >50 vol %, >60 vol %, >70 vol %, >80 vol %, >90 vol %, >95 vol %, >96 vol %, >97 vol %, >98 vol %, or >99 vol %) the stream discharged through the liquid-phase product outlet is pressurized with a pump and then returns to the first reaction bed of the reactor as the recycled stream and is mixed with the fresh alkylation raw material, the minority thereof is sent to a product separation device such as a fractionating column, the separated alkylation oil is used as the product of the apparatus.

The spent catalyst is subjected to the regeneration reaction in the catalyst regenerator to recover the activity; the manner of regeneration is not particularly limited, and the regeneration can be performed under normal regeneration conditions. The regeneration medium may be an oxygen-containing atmosphere or a hydrogen-containing atmosphere. Specifically, the regeneration may be performed in an oxygen-containing atmosphere or may be performed in a hydrogen-containing atmosphere.

The oxygen-containing atmosphere contains oxygen gas and inert gas and can be air, or a mixed gas of oxygen gas and nitrogen gas. In the oxygen-containing atmosphere, the content of oxygen gas can be 0.5-20% by volume. In addition, the content of oxygen gas can also be adjusted according to the regeneration process. The regeneration is performed in an oxygen-containing atmosphere, and the regeneration can be performed at a temperature of 180-500° C. or 200-500° C.; during regeneration, the pressure in the reactor can be 0.01-0.5 MPa, and the pressure is gauge pressure.

The hydrogen-containing atmosphere may contain hydrogen gas and C4 liquefied gas, and the content of hydrogen gas is 70-99% by volume. The regeneration is performed in a hydrogen-containing atmosphere, the regeneration can be performed at a temperature of 100-400° C., preferably 180-280° C.; during regeneration, the pressure in the reactor can be 0.1-5 MPa, preferably 0.5-3.5 MPa, the pressure is gauge pressure.

Preferably, the superficial flow velocity of the regeneration medium in the catalyst regenerator is 0.003-0.8 m/s, further preferably 0.02-0.5 m/s.

The liquid-solid radial moving bed reaction apparatus provided by the present invention has a simple structure and is suitable for the solid acid alkylation reaction, and the alkylation reaction and the solid acid catalyst regeneration can be performed simultaneously without mutual interference. The component-based mixer is arranged out of the radial moving bed so that the space in the radial moving bed reactor is saved, the fresh feedstock and the recycled stream are fully and uniformly mixed, the selectivity of the alkylation reaction is improved, the superposition reaction of alkene is reduced, the space in the reactor is saved, and the reaction efficiency is improved.

In the second aspect, the present invention provides a solid acid alkylation reaction and regeneration process, the process uses a liquid-solid radial moving bed reaction apparatus, an alkylation raw material and a recycled stream are mixed with the component-based mixer and enter the radial moving bed reactor in one or more sections; the liquid-phase mixed stream, after the distribution with the reaction stream distribution zone, passes through the catalyst bed along the radial direction from the inside to the outside or from the outside to the inside, contacts with the solid acid catalyst to perform the reaction, and the liquid-phase mixed stream-after-the-reaction reaches the stream collection zone, and is discharged through the stream-after-the-reaction withdrawing pipe, and used as the recycled stream or further separated to produce the alkylation oil product (the discharged stream-after-the-reaction, is mixed with the fresh feedstock by the component-based mixer, and then sent into the next reaction bed to continue to participate in the reaction, or is discharged off the reactor, an alkylation oil product is obtained by separation); the solid acid catalyst in the catalyst bed of the radial moving bed reactor gradually deactivates, falls bed by bed, finally falls to the bottom catalyst-collecting area, and leaves the radial moving bed reactor; then enters the spent catalyst receiver, in which the liquid-phase mixed stream carried in the catalyst is removed, via the catalyst delivery pipeline, subsequently flows into the catalyst regenerator to perform the regeneration reaction, is regenerated in an oxygen atmosphere or in the presence of hydrogen gas to recover the activity; the regenerated catalyst with recovered activity at the bottom of the catalyst regenerator flows into the regenerated catalyst receiver, and the liquid-phase mixed stream is introduced thereto to replace and remove the gas in the gap of the regenerated catalyst, and then the regenerated catalyst returns to the radial moving bed reactor via the catalyst delivery conduit for the continuous reaction;

The liquid-solid radial moving bed reaction apparatus comprises: a radial moving bed reactor, a spent catalyst receiver, a catalyst regenerator, and a regenerated catalyst receiver that are successively connected, wherein the catalyst discharging outlet of the regenerated catalyst receiver is communicated with the catalyst inlet of the radial moving bed reactor; a reaction stream distribution zone, a catalyst bed, and a stream-after-the-reaction collection zone are arranged in the radial moving bed reactor from the inside to the outside or from the outside to the inside, the reaction stream distribution zone is communicated with the reaction stream feeding pipeline; the stream-after-the-reaction collection zone is communicated with the stream-after-the-reaction withdrawing pipe;

A component-based mixer is arranged on the reaction stream feeding pipeline; the component-based mixer consists of an upper recycled stream pipe, a lower reaction stream feeding pipe, and a fresh feedstock feeding pipe extending into the reaction stream feeding pipeline, a nozzle of the feeding pipe is arranged at the outlet of the fresh feedstock feeding pipe, a filler and/or a mixing fin is arranged in the reaction stream feeding pipeline, wherein the component-based mixer is located out of the radial moving bed reactor.

For the component-based mixer arranged on the reaction stream feeding pipeline, the upper recycled stream pipe and the lower reaction stream feeding pipe are composed of one pipe or composed of the identical or different pipes, preferably composed by connecting identical pipes; the nozzle of the feeding pipe arranged at the outlet of the fresh feedstock feeding pipe has an upward opening direction with an angle inclined relative to the axis direction of the pipeline of no greater than 60 degrees, 50 degrees, 40 degrees, 30 degrees, 20 degrees, 10 degrees, 5 degrees or 0 degrees; the filler and/or the mixing fin are preferably arranged in the lower reaction stream feeding pipe.

In an embodiment according to the solid acid alkylation reaction and regeneration process of the present invention, the radial moving bed reactor is provided with at least two reaction beds arranged up and down, a catalyst delivery pipe is arranged between two adjacent reaction beds, so that the catalyst can move in the radial moving bed reactor from top to bottom; a reaction stream space is further arranged between two reaction beds, the reaction stream distribution zone is communicated through the reaction stream space with the reaction stream feeding pipeline; the component-based mixer is arranged on the reaction stream feeding pipeline of each reaction bed.

In an embodiment according to the solid acid alkylation reaction and regeneration process of the present invention, at least one reaction bed and at least one regeneration bed are arranged up and down in the radial moving bed reactor, so that the catalyst can move in the radial moving bed reactor from top to bottom, preferably, the number of the reaction bed(s) is 2-8, for example, 4-8, the number of the regeneration bed(s) is 2-8, for example, 4-8, preferably 2-7, for example, 4-7; more preferably, the number of the regeneration bed(s) and the number of the reaction bed(s) are identical and one regeneration bed is arranged immediately below each reaction bed, or more preferably, the number of the regeneration bed is less than the number of the reaction bed by one, the reaction bed and the regeneration bed are intervally successively arranged, and the reaction beds are arranged both at the top and the bottom of the radial moving bed reactor;

Each reaction bed comprises a reaction stream distribution zone, a catalyst bed, and a stream-after-the-reaction collection zone, and each reaction bed has a reaction stream feeding pipeline and a stream-after-the-reaction withdrawing pipe, the reaction stream distribution zone is communicated through the reaction stream space with the reaction stream feeding pipeline, the stream-after-the-reaction collection zone is communicated with the stream-after-the-reaction withdrawing pipe, the component-based mixer is arranged on the reaction stream feeding pipeline of each reaction bed;

The regeneration bed has a similar physical structure to the reaction bed, namely, each regeneration bed correspondingly comprises a regeneration medium distribution zone, a catalyst bed, and a regeneration medium collection zone, and each regeneration bed has a regeneration medium feeding pipe and a regeneration medium withdrawing pipe, the regeneration medium distribution zone is communicated via the regeneration medium space with the regeneration medium feeding pipe, the regeneration medium collection zone is communicated with the regeneration medium withdrawing pipe;

Any two adjacent beds of the reaction bed(s) and the regeneration bed(s) are communicated through the catalyst delivery pipe; the catalyst in the reaction bed and the catalyst in the regeneration bed fall through the catalyst delivery pipe from the upstream bed to the adjacent downstream bed, finally, fall to the bottom catalyst-collecting area, and leave the radial moving bed reactor; Preferably, the regeneration medium feeding pipe of any regeneration bed except the first regeneration bed can be the regeneration medium withdrawing pipe of the previous regeneration bed (upstream bed) or can be communicated with the regeneration medium withdrawing pipe of the previous regeneration bed (upstream bed).

In an embodiment according to the solid acid alkylation reaction and regeneration process of the present invention, an L-shaped or approximately L-shaped stream delivery valve manifold is arranged on the pipeline between the catalyst discharging outlet at the bottom of the radial moving bed reactor and the spent catalyst receiver, the discharge rate of the catalyst is regulated by changing the flow of the liquid-phase mixed stream into the valve manifold. Thereby the falling rate and the residence time in each reaction bed of the catalyst in the reactor can be controlled and adjusted.

In an embodiment according to the solid acid alkylation reaction and regeneration process of the present invention, a top catalyst collection zone is arranged at the top of the radial moving bed reactor, the catalyst inlet is communicated through the top catalyst collection zone with the catalyst delivery pipe.

In an embodiment according to the solid acid alkylation reaction and regeneration process of the present invention, the catalyst delivery pipes are respectively arranged between two adjacent beds, between the top catalyst collection zone and the first bed, and between the last bed and the bottom catalyst-collecting area.

In an embodiment according to the solid acid alkylation reaction and regeneration process of the present invention, in the radial moving bed reactor, the recycled stream pipe of the component-based mixer of the next reaction bed is the stream-after-the-reaction withdrawing pipe of the previous reaction bed or is communicated with the stream-after-the-reaction withdrawing pipe of the previous reaction bed.

In an embodiment according to the solid acid alkylation reaction and regeneration process of the present invention, catalyst circulation pipelines for connecting the spent catalyst receiver, catalyst regenerator, and the regenerated catalyst receiver are arranged vertically or inclined at an angle relative to the horizontal plane of not less than 40 degrees.

In an embodiment according to the solid acid alkylation reaction and regeneration process of the present invention, the catalyst regenerator or the regenerated catalyst receiver is further provided with a fresh catalyst charging inlet.

In an embodiment according to the solid acid alkylation reaction and regeneration process of the present invention, a regeneration medium inlet is arranged at the upper part of the catalyst regenerator, a regeneration medium outlet is arranged at the bottom of or the bottom discharging pipeline of the catalyst regenerator; the regeneration medium inlet is positioned at 70% or higher of the straight-tube segment of the catalyst regenerator from bottom to top, the regeneration medium outlet is positioned at 20% or lower of the straight-tube segment of the catalyst regenerator from bottom to top, preferably, arranged on the bottom discharging pipeline. Preferably the pipeline starting from the regeneration medium outlet of the catalyst regenerator is further provided with a filter. The filter is used to block the catalyst of the regenerator from flowing into the downstream gas circulation pressurizing equipment and to collect the fine powder or fine particles generated during the regeneration process due to friction or purging.

In an embodiment according to the solid acid alkylation reaction and regeneration process of the present invention, a liquid-phase mixed stream discharging outlet is arranged at the bottom of or the bottom discharging pipeline of the spent catalyst receiver; the regenerated catalyst receiver and/or the pipeline introduced into the regenerated catalyst receiver are/is provided with a liquid-phase mixed stream charging inlet. Through the liquid-phase mixed stream discharging outlet and the liquid-phase mixed stream charging inlet, the liquid-phase mixed stream carried in the catalyst is evacuated or the liquid-phase mixed stream is added to the regenerated catalyst.

In an embodiment according to the solid acid alkylation reaction and regeneration process of the present invention, in the component-based mixer, the ratio of the cross-sectional area of the fresh feedstock feeding pipe to the cross-sectional area of the recycled stream pipe is 0.001-0.5:1, preferably 0.002-0.1:1.

In an embodiment according to the solid acid alkylation reaction and regeneration process of the present invention, the filler and/or the mixing fin for intensifying the mixing of the stream is arranged in the feeding pipe of the component-based mixer (namely the upper recycled stream pipe and the lower reaction stream feeding pipe), preferably, arranged in the lower reaction stream feeding pipe. The filler is selected from flow guide plate, fin, regular filler, or random filler, preferably a group of inclined fins is arranged.

In an embodiment according to the solid acid alkylation reaction and regeneration process of the present invention, the alkylation raw material is a hydrocarbon fraction containing alkenes and alkanes, preferably C4 fraction containing C4 alkene and C4 alkane, more preferably a mixture of C4 alkene and C4 alkane. In an embodiment, the alkylation raw material is a hydrocarbon fraction containing alkene and alkane, wherein the mole ratio of alkane to alkene is 5-50:1, for example, 10-40:1 or 20-30:1. In an embodiment, the alkylation raw material is a hydrocarbon fraction containing C3-C5 alkene and C3-C5 alkane, wherein the mole ratio of alkane to alkene is 5-50:1, for example, 10-40:1 or 20-30:1. In an embodiment, the alkylation raw material is a mixture of C3-C5 alkene and C3-C5 alkane, wherein the mole ratio of alkane to alkene is 5-50:1, for example, 10-40:1 or 20-30:1.

In an embodiment according to the solid acid alkylation reaction and regeneration process of the present invention, in the radial moving bed reactor, the reaction temperature is 30-100° C., the superficial flow velocity of the liquid-phase mixed stream in the reactor is 0.05-1 m/s; the weight hourly space velocity of the mixed alkene feedstock is 0.05-1 $h^{-1}$; the mole ratio of alkane to alkene at the inlet of the reaction bed is 200-1000:1; the average particle diameter of the catalyst particles is 0.3-3 mm In an embodiment according to the solid acid alkylation reaction and regeneration process of the present invention, the catalyst is a solid acid catalyst, containing a molecular sieve and a heat-resistant inorganic oxide, based on the total amount of the solid acid catalyst, the content of the molecular sieve is 65-95 wt %, the content of the heat-resistant inorganic oxide is 5-35 wt %; preferably, the molecular sieve is selected from at least one of FAU structure zeolite, BETA structure zeolite, and MFI structure zeolite, the heat-resistant inorganic oxide is alumina and/or silica; Further preferably, the solid acid catalyst also contains a metal active component, the metal active component is selected from at least one of Fe, Co, Ni, Pd, and Pt, based on the total amount of the solid acid catalyst, the content of the metal active component is 0.15-2 wt %.

In an embodiment according to the solid acid alkylation reaction and regeneration process of the present invention, the spent catalyst is subjected to the regeneration reaction in the catalyst regenerator to recover the activity, the regeneration manner is not particularly limited, and the regeneration can be performed under normal regeneration conditions. The regeneration medium may be an oxygen-containing atmosphere or a hydrogen-containing atmosphere. Specifically, the regeneration may be performed in an oxygen-containing atmosphere or may be performed in a hydrogen-containing atmosphere.

In an embodiment according to the solid acid alkylation reaction and regeneration process of the present invention, in the catalyst regenerator, the spent catalyst and an oxygen-containing gas are subjected to the oxidizing reaction at 180-500° C. or 200-500° C., under the pressure of 0.01-0.5 MPa (gauge pressure), the carbon deposited on the spent catalyst is removed to recover the activity of the catalyst. The oxygen-containing gas contains oxygen gas and inert gas and can be air, or a mixed gas of oxygen gas and nitrogen gas. In the oxygen-containing gas, the content of oxygen gas can be 0.5-20% by volume. In addition, the content of oxygen gas can also be adjusted according to the regeneration process.

In an embodiment according to the solid acid alkylation reaction and regeneration process of the present invention, in the catalyst regenerator, the spent catalyst is subjected to the regeneration reaction in a hydrogen-containing atmosphere, the hydrogen-containing atmosphere may contain hydrogen gas and C4 liquefied gas, and the content of hydrogen gas is 70-99% by volume. The regeneration is performed in a hydrogen-containing atmosphere, the regeneration can be performed at a temperature of 100-400° C., preferably 180-280° C.; during regeneration, the pressure in the reactor can be 0.1-5 MPa, preferably 0.5-3.5 MPa, the pressure is gauge pressure.

In an embodiment according to the solid acid alkylation reaction and regeneration process of the present invention, the superficial flow velocity of the regeneration medium in the catalyst regenerator is 0.003-0.8 m/s, preferably 0.02-0.5 m/s.

In an embodiment according to the solid acid alkylation reaction and regeneration process of the present invention, in the radial moving bed reactor, at least two reaction beds are vertically arranged up and down, preferably, the radial moving bed reactor contains 4-8 reaction beds. Every reaction beds, from the inside to the outside, or from the outside to the inside, all contain a reaction stream feeding pipeline, a reaction stream distribution zone, a ring-column shaped catalyst bed, a stream-after-the-reaction collection zone, and a stream-after-the-reaction withdrawing pipe (for withdrawing the stream-after-the-reaction). A top catalyst collection zone is arranged at the top of the radial moving bed reactor, and catalyst delivery pipes are arranged between the top catalyst collection zone and the first catalyst bed, between the upstream and downstream catalyst beds, and between the last catalyst bed and the bottom catalyst-collecting area. The catalyst inlet is communicated with the top catalyst collection zone and the catalyst delivery pipe, and the catalyst delivery pipe at the reactor bottom is communicated with the bottom catalyst-collecting area and the catalyst discharging outlet.

In an embodiment according to the solid acid alkylation reaction and regeneration process of the present invention, an L-shaped or approximately L-shaped stream delivery valve manifold is arranged on the pipeline between the catalyst discharging outlet and the spent catalyst receiver, and the discharge rate of the catalyst is regulated by changing the flow of the liquid-phase mixed stream into the valve manifold. Thereby the falling rate and the residence time in each reaction bed of the catalyst in the reactor can be controlled and adjusted.

In an embodiment according to the solid acid alkylation reaction and regeneration process of the present invention, the component-based mixer can be arranged on the pipeline between the stream-after-the-reaction withdrawing pipe of the previous reaction bed and the reaction stream feeding pipe of the next reaction bed, and the fresh feedstock feeding pipe is used as a supplemental fresh feedstock inlet.

In an embodiment according to the solid acid alkylation reaction and regeneration process of the present invention, a fresh alkylation raw material and a recycled stream are mixed with the component-based mixer and enter the radial moving bed reactor in one or more sections; the liquid-phase mixed stream, after the distribution with the reaction stream distribution zone, passes through the catalyst bed along the radial direction, contacts with the solid acid catalyst to perform the reaction, and the liquid-phase mixed stream-after-the-reaction reaches the stream collection zone, and is discharged through the stream-after-the-reaction withdrawing pipe, and used as the recycled stream or further separated to produce the alkylation oil product (the discharged stream-after-the-reaction, is mixed with the fresh feedstock by the component-based mixer, and then sent into the next reaction bed to continue to participate in the reaction, or is discharged off the reactor, an alkylation oil product is obtained by separation); the solid acid catalyst in the catalyst bed gradually deactivates, falls bed by bed, finally falls to the bottom catalyst-collecting area, and leaves the radial moving bed reactor; then enters the spent catalyst receiver, in which the liquid-phase mixed stream carried in the catalyst is removed, via the catalyst delivery pipeline, subsequently flows into the catalyst regenerator to perform the regeneration reaction, is regenerated in an oxygen atmosphere or in the presence of hydrogen gas to recover the activity; the regenerated catalyst with recovered activity at the bottom of the catalyst regenerator flows into the regenerated catalyst receiver, and the liquid-phase mixed stream is introduced thereto to replace and remove the gas in the gap of the regenerated catalyst, and then the regenerated catalyst returns to the radial moving bed reactor via the catalyst delivery conduit for the continuous reaction, the catalyst continues to participate in the reaction until it is deactivated and delivered to the spent catalyst receiver, and the process is circulated in this manner.

In an embodiment according to the solid acid alkylation reaction and regeneration process of the present invention, a spent catalyst buffer tank is arranged below/after the radial moving bed reactor to preserve the spent catalyst discharged from the reactor during the periods of withdrawing the liquid-phase mixed stream from the spent catalyst receiver and discharging the catalyst to the catalyst regenerator, ensuring the catalyst stream flow continuity in the radial moving bed reactor and the smoothness of the apparatus operation.

In an embodiment according to the solid acid alkylation reaction and regeneration process of the present invention, the spent catalyst receiver, the catalyst regenerator, and the regenerated catalyst receiver are successively arranged from top to bottom, catalyst circulation pipelines for connecting the spent catalyst receiver, the catalyst regenerator, and the regenerated catalyst receiver are arranged vertically or inclined at an angle relative to the horizontal plane of not less than 40 degrees, which is convenient for the smooth flow of the catalyst particle stream from top to bottom, and prevents the stream from accumulating or remaining in the pipeline, which affects the valve sealing performance or the catalyst regeneration effect.

In an embodiment according to the solid acid alkylation reaction and regeneration process of the present invention, the stream-after-the-reaction withdrawing pipe of the last reaction bed of the radial moving bed reactor is used as the liquid-phase product outlet, the majority of (for example, >50 vol %, >60 vol %, >70 vol %, >80 vol %, >90 vol %, >95 vol %, >96 vol %, >97 vol %, >98 vol %, or >99 vol %) the stream discharged through the liquid-phase product outlet is pressurized with a pump and then returns to the first reaction bed of the reactor as the recycled stream and is mixed with the fresh alkylation raw material, the minority thereof is sent to a product separation device such as a fractionating column, the separated alkylation oil is used as the product of the apparatus.

In an embodiment according to the solid acid alkylation reaction and regeneration process of the present invention, the catalyst regenerator is provided with a fresh catalyst charging inlet. By providing the catalyst regenerator with the fresh catalyst charging inlet, a part of the catalyst that has lost its activity or the catalyst that is difficult to restore the initial activity can be replaced with a fresh catalyst to ensure the processing capacity of the apparatus.

In an embodiment according to the solid acid alkylation reaction and regeneration process of the present invention, a liquid-phase mixed stream discharging outlet is arranged at the bottom of or the bottom discharging pipeline of the spent catalyst receiver; the regenerated catalyst receiver or the pipeline introduced into the regenerated catalyst receiver is provided with a liquid-phase mixed stream charging inlet. Through the liquid-phase mixed stream discharging outlet and the liquid-phase mixed stream charging inlet, the liquid-phase mixed stream carried in the catalyst is evacuated or the liquid-phase mixed stream is added to the regenerated catalyst.

In the solid acid alkylation process in the prior art, if the streams are not uniformly mixed, there is a problem that alkene is easy to perform the superposition side reaction, and the product selectivity and the catalyst treatment capacity are influenced. The present invention adopts the liquid-solid radial moving bed reaction apparatus, the recycled stream, and the fresh alkylation raw material firstly pass through the component-based mixer to complete the mixing process outside the liquid-solid moving bed reactor, and the mixed reaction stream enters the reaction beds through the reaction stream feeding pipeline in one or more sections to contact with the catalyst for the reaction. The uniform stream mixing guarantees the mixing effect, saves space in the reactor, and solves the problem of the uneven mixing of the fresh alkylation raw material and the recycled stream in the prior art.

The endpoints of the ranges and any values disclosed herein are not limited to the precise ranges or values, and these ranges or values should be understood to include the values close to these ranges or values. For numerical ranges, the endpoints of the ranges to each other, the endpoints of the ranges and the individual point values, and the individual point values to each other can be combined to give one or more new numerical ranges, and these new numerical ranges should be construed as specifically disclosed herein.

In the present invention, if no explanation is made to the contrary, the directional words used such as "above" and "below" usually refer to "above" and "below" as shown with reference to the drawings. The orientation words used such as "in", "inside", "out" and "outside" refer to the inner and outer part relative to the contour of each component itself.

In the present invention, "above the bed", "the top of the bed", or the like refers to being located at 70% or higher of each bed from bottom to top, and "the bottom of the bed", or the like refers to being located at 20% or lower of each bed from bottom to top.

In the present invention, the expression "successively connected" means that, for example, the catalyst outlet of the radial moving bed reactor 1 is connected to the catalyst inlet of the spent catalyst receiver 5, the catalyst outlet of the spent catalyst receiver 5 is connected to the catalyst inlet of the catalyst regenerator 4, the catalyst outlet of the catalyst regenerator 4 is connected to the catalyst inlet of the regenerated catalyst receiver 6. The catalyst outlet of the regenerated catalyst receiver 6 is communicated with the catalyst inlet of the radial moving bed reactor 1 to send the regenerated catalyst into the radial moving bed reactor 1.

In addition, the present invention also provides a group of the following technical solutions:

1. A liquid-solid radial moving bed reaction apparatus, which is characterized in that the apparatus comprises:

A radial moving bed reactor, a spent catalyst receiver, a catalyst regenerator and a regenerated catalyst receiver that are successively connected, wherein a catalyst outlet of the regenerated catalyst receiver is communicated with a catalyst inlet of the radial moving bed reactor; a reaction stream distribution zone, a catalyst bed and a stream-after-the-reaction collection zone are arranged in the radial moving bed reactor from the inside to the outside or from the outside to the inside, the reaction stream distribution zone is communicated with a feeding pipe; the stream-after-the-reaction collection zone is communicated with a stream-after-the-reaction withdrawing pipe; a component-based mixer is arranged on the feeding pipe; the component-based mixer consists of an upper recycled stream pipeline, a lower feeding pipe and a fresh feedstock feeding pipe extending into the feeding pipe, a nozzle of the feeding pipe is arranged at an outlet of the fresh feedstock feeding pipe, a filler and/or a mixing fin is arranged in the feeding pipe.

2. The liquid-solid radial moving bed reaction apparatus according to technical solution 1, which is characterized in that the radial moving bed reactor is provided with at least two reaction beds, a catalyst delivery pipe is arranged between two adjacent reaction beds so that the catalyst can move in the radial moving bed reactor from top to bottom; a reaction stream space is arranged between two reaction beds, the reaction stream distribution zone is communicated with the feeding pipe via the reaction stream space; the feeding pipe of each reaction bed is provided with the component-based mixer.

3. The liquid-solid radial moving bed reaction apparatus according to technical solution 2, which is characterized in that an L-shaped or approximately L-shaped stream delivery valve manifold is arranged on the pipeline between the catalyst outlet at the bottom of the radial moving bed reactor and the spent catalyst receiver, the discharge rate of the catalyst is regulated by changing the flow of the liquid-phase stream into the valve manifold.

4. the liquid-solid radial moving bed reaction apparatus according to technical solution 2 or 3, which is characterized in that a top catalyst collecting chamber is provided at the top of the radial moving bed reactor, and the catalyst inlet is communicated with the catalyst delivery pipe via the top catalyst collecting chamber.

5. The liquid-solid radial moving bed reaction apparatus according to technical solution 2, which is characterized in that in the radial moving bed reactor, the stream circulation pipeline of the component-based mixer of the next reaction bed is the stream withdrawing pipeline of the previous reaction bed.

6. The liquid-solid radial moving bed reaction apparatus according to technical solution 1, which is characterized in that catalyst circulation pipelines for connecting the spent catalyst receiver, catalyst regenerator, and the regenerated catalyst receiver are arranged vertically or inclined at an angle relative to the horizontal plane of not less than 40 degrees.

7. The liquid-solid radial moving bed reaction apparatus according to technical solution 1, which is characterized in that the catalyst regenerator is further provided with a fresh catalyst charging inlet.

8. The liquid-solid radial moving bed reaction apparatus according to technical solution 1 or 2, which is characterized in that a regeneration medium inlet is arranged at the upper part of the catalyst regenerator, a regeneration medium outlet is arranged at the bottom of or the bottom discharging pipeline of the catalyst regenerator; the regeneration medium inlet is positioned at 70% or higher of the straight-tube segment of the catalyst regenerator from bottom to top, the regeneration medium outlet is positioned at 20% or lower of the straight-tube segment of the catalyst regenerator from bottom to top.

9. The liquid-solid radial moving bed reaction apparatus according to technical solution 1, which is characterized in that the pipeline starting from the regeneration medium outlet is further provided with a filter.

10. The liquid-solid radial moving bed reaction apparatus according to technical solution 1 or 2, which is characterized in that a catalyst discharging outlet is arranged at the bottom of or the bottom discharging pipeline of the spent catalyst receiver.

11. The liquid-solid radial moving bed reaction apparatus according to technical solution 1, which is characterized in that in the component-based mixer, the ratio of the cross-sectional area of the fresh feedstock feeding pipe to the cross-sectional area of the stream circulation tube is 0.001-0.5:1.

12. The liquid-solid radial moving bed reaction apparatus according to technical solution 11, which is characterized in that in the component-based mixer, the ratio of the cross-sectional area of the fresh feedstock feeding pipe to the cross-sectional area of the stream circulation tube is 0.002-0.1:1. In addition, the present invention also provides another group of the following technical solutions:

1. A solid acid alkylation process, which is characterized in that a liquid-solid radial moving bed reaction apparatus is used, an alkylation raw material and a recycled stream are mixed with the component-based mixer and enter the radial moving bed reactor; the mixed stream passes through the catalyst bed along the radial direction, contacts with the solid acid catalyst to perform the reaction, and the mixed stream-after-the-reaction reaches the stream collection zone, and is used as the recycled stream or further separated to produce the alkylation oil product; the solid acid catalyst in the catalyst bed of the radial moving bed reactor gradually deactivates, falls to the catalyst-collecting area, leaves the radial moving bed reactor, enters the spent catalyst receiver, in which the liquid-phase stream carried in the catalyst is removed, subsequently flows into the catalyst regenerator to perform the regeneration reaction, the regenerated catalyst with recovered activity flows into the regenerated catalyst receiver, in which the gas therein is replaced and removed, and returns to the radial moving bed reactor for continuous reaction;

The liquid-solid radial moving bed reaction apparatus comprises: a radial moving bed reactor, a spent catalyst receiver, a catalyst regenerator and a regenerated catalyst receiver that are successively connected, wherein the catalyst outlet of the regenerated catalyst receiver is communicated with the catalyst inlet of the radial moving bed reactor; a reaction stream distribution zone, a catalyst bed and a stream-after-the-reaction collection zone are arranged in the radial moving bed reactor from the inside to the outside or from the outside to the inside, the reaction stream distribution zone is communicated with the feeding pipe; the stream-after-the-reaction collection zone is communicated with the stream-after-the-reaction withdrawing pipe; a component-based mixer is arranged on the feeding pipe, the component-based mixer consists of an upper recycled stream pipeline, a lower feeding pipe and a fresh feedstock feeding pipe extending into the feeding pipe, the nozzle of the feeding pipe is arranged at the outlet of the fresh feedstock feeding pipe, a filler and/or a mixing fin is arranged in the feeding pipe.

2. The solid acid alkylation process according to technical solution 1, which is characterized in that the radial moving bed reactor is provided with at least two reaction beds, a catalyst delivery pipe is arranged between two adjacent reaction beds, so that the catalyst can move in the radial moving bed reactor from top to bottom; a reaction stream space is arranged between two reaction beds, the reaction stream distribution zone is communicated with the feeding pipe via the reaction stream space; the feeding pipe of each reaction bed is provided with the component-based mixer.

3. The solid acid alkylation process according to technical solution 2, which is characterized in that an L-shaped or approximately L-shaped stream delivery valve manifold is arranged on the pipeline between the catalyst outlet at the bottom of the radial moving bed reactor and the spent catalyst receiver, the discharge rate of the catalyst is regulated by changing the flow of the liquid-phase stream into the valve manifold.

4. The solid acid alkylation process according to technical solution 2 or 3, which is characterized in that a top catalyst collecting chamber is provided at the top of the radial moving bed reactor, and the catalyst inlet is communicated with the catalyst delivery pipe via the top catalyst collecting chamber.

5. The solid acid alkylation process according to technical solution 2, which is characterized in that in the radial moving bed reactor, the stream circulation pipeline of the component-based mixer of the next reaction bed is the stream withdrawing pipeline of the previous reaction bed.

6. The solid acid alkylation process according to technical solution 1, which is characterized in that catalyst circulation pipelines for connecting the spent catalyst receiver, catalyst regenerator, and the regenerated catalyst receiver are arranged vertically or inclined at an angle relative to the horizontal plane of not less than 40 degrees.

7. The solid acid alkylation process according to technical solution 1, which is characterized in that the catalyst regenerator or the regenerated catalyst receiver is further provided with a fresh catalyst charging inlet.

8. The solid acid alkylation process according to technical solution 1 or 2, which is characterized in that a regeneration medium inlet is arranged at the upper part of the catalyst regenerator, a regeneration medium outlet is arranged at the bottom of or the bottom discharging pipeline of the catalyst regenerator; the regeneration medium inlet is positioned at 70% or higher of the straight-tube segment of the catalyst regenerator from bottom to top, the regeneration medium outlet is positioned at 20% or lower of the straight-tube segment of the catalyst regenerator from bottom to top.

9. The solid acid alkylation process according to technical solution 8, which is characterized in that the pipeline starting from the regeneration medium outlet is further provided with a filter.

10. The solid acid alkylation process according to technical solution 1 or 2, which is characterized in that a liquid-phase stream outlet is arranged at the bottom of or the bottom discharging pipeline of the spent catalyst receiver.

11. The solid acid alkylation process according to technical solution 1 or 2, which is characterized in that in the component-based mixer, the ratio of the cross-sectional area of the fresh feedstock feeding pipe to the cross-sectional area of the stream circulation tube is 0.001-0.5:1, preferably 0.002-0.1:1.

12. The solid acid alkylation process according to technical solution 1 or 2, which is characterized in that the alkylation raw material is a hydrocarbon fraction containing alkenes and alkanes.

13. The solid acid alkylation process according to technical solution 1 or 2, which is characterized in that in the radial moving bed reactor, the reaction temperature is 30° C.-100° C., the superficial flow velocity of the mixed stream in the reactor is 0.05-1 m/s; the weight hourly space velocity of the alkene feedstock is 0.05-1 $h^{-1}$; the mole ratio of alkane to alkene is 200-1000:1; the average particle diameter of the solid acid catalyst particles is 0.3-3 mm 14. The solid acid alkylation process according to technical solution 1 or 2, which is characterized in that the catalyst is a solid acid catalyst, containing 95 wt %-65 wt % of a molecular sieve and 5 wt %-35 wt % of a heat-resistant inorganic oxide, wherein the molecular sieve is selected from one or more of FAU structure zeolite, BETA structure zeolite, and MFI structure zeolite, the heat-resistant inorganic oxide is alumina and/or silica.

15. The solid acid alkylation process according to technical solution 1 or 2, which is characterized in that in the catalyst regenerator, the spent catalyst and an oxygen-containing gas are subjected to the oxidizing reaction under the conditions of the temperature being 200-500° C. and the pressure being 0.01-0.5 MPa, the carbon deposited on the spent catalyst is removed to recover the activity of the catalyst.

16. The solid acid alkylation process according to technical solution 1 or 2, which is characterized in that in the catalyst regenerator, the spent catalyst is contacted with a hydrogen gas-containing regeneration medium to perform the reaction, the carbon deposited on the spent catalyst is removed to recover the activity of the catalyst, the regeneration temperature is 100-400° C., the regeneration pressure is 0.5-3.5 MPa.

Regarding the drawings, the structure of the liquid-solid radial alkylation reaction apparatus and the specific steps of the solid acid alkylation process provided by the present invention are specifically illustrated.

FIG. 1 is a schematic diagram of the liquid-solid radial moving bed reaction apparatus provided by the present invention. As shown in FIG. 1, the liquid-solid radial moving bed reaction apparatus comprises the radial moving bed reactor 1, the spent catalyst receiver 5, the catalyst regenerator 4, and the regenerated catalyst receiver 6 that are successively connected, wherein the catalyst discharging outlet 36 of the regenerated catalyst receiver 6 is communicated with the catalyst inlet 24 of the radial moving bed reactor; The radial moving bed reactor 1 is provided with three reaction beds, and three catalyst beds are connected by the catalyst delivery pipes 16.

Each reaction bed, from the outside to the inside, is provided with a reaction stream distribution zone 12, a ring-column shaped catalyst bed 3, and a stream-after-the-reaction collection zone 11, The reaction stream distribution zone 12 is communicated with the reaction stream feeding pipeline; the stream-after-the-reaction collection zone 11 is communicated with the stream-after-the-reaction withdrawing pipe 13; Between two adjacent reaction beds, and between the first reaction bed and the top catalyst collection zone 10 are arranged the reaction stream space 2 communicated with the reaction stream distribution zone 12 and catalyst delivery pipes 16 communicated with the top catalyst collection zone 10 or each catalyst bed, the stream-after-the-reaction withdrawing pipe 13 communicated with the stream-after-the-reaction collection zone, and the reaction stream feeding pipeline communicated with the reaction stream space 2;

The catalyst feeding inlet 24 is communicated with the top catalyst collection zone 10, and communicated with the catalyst discharging outlet 23 via the catalyst delivery pipe 16 and the bottom catalyst-collecting area 14.

The component-based mixers are arranged on the reaction stream feeding pipelines of every reaction beds, and the stream-after-the-reaction withdrawing pipes 13 of the first, second, and third reaction beds are respectively used as the recycled stream pipes in the component-based mixers in the reaction stream feeding pipelines of the second, third and first reaction beds;

The fresh feedstock feeding pipe 17 is used as the supplemental fresh feedstock inlet.

On the communication pipeline of the catalyst outlet of the radial moving bed reactor 1 and the catalyst inlet of the spent catalyst receiver 5 is arranged the first particle flow regulator 25 to adjust the flow of catalyst particles.

The spent catalyst receiver 5 (preferably the bottom) is provided with the liquid-phase mixed stream discharging outlet 29. According to the present invention, the liquid-phase stream carried in the catalyst can be removed by directly reducing the pressure or increasing the pressure by introducing high-pressure hydrogen, nitrogen, and the like in the spent catalyst receiver 5, and the liquid-phase stream can be discharged through the liquid-phase mixed stream discharging outlet 29. Preferably, a removed liquid filter 7 is arranged on the delivery pipeline for withdrawing the liquid-phase stream starting from the liquid-phase mixed stream discharging outlet 29. The removed liquid filter 7 is used to block fine catalyst powder or fine catalyst particles.

The liquid-withdrawn catalyst in the spent catalyst receiver 5 is introduced into the catalyst regenerator 4 for regeneration, and the catalyst regenerator 4 is provided with a regeneration medium inlet 30 and a regeneration medium outlet 31. The regeneration medium is introduced into the catalyst regenerator 4 through the regeneration medium inlet 30 and contacted with the catalyst for the regeneration of the catalyst, and the regeneration medium is discharged through the regeneration medium outlet 31. On the regeneration medium delivery pipeline starting from the regeneration medium outlet 31 is arranged a medium-after-regeneration filter 8 to block the fine powder or the fine particles. The catalyst regenerator 4 can also be provided with a fresh catalyst feeding inlet for the fresh catalyst to enter the catalyst regenerator 4. By providing the catalyst regenerator 4 with the fresh catalyst feeding inlet, a part of the catalyst that has lost its activity or the catalyst that is difficult to restore the initial activity can be replaced with a fresh catalyst to ensure the processing capacity of the apparatus.

The regenerated catalyst flows into the regenerated catalyst receiver 6 through the catalyst delivery pipeline at the bottom of the catalyst regenerator 4, and the regenerated catalyst receiver 6 is provided with a liquid-phase mixed stream charging inlet 32. A liquid-phase stream is introduced to the regenerated catalyst receiver 6 through the liquid-phase mixed stream charging inlet 32 to replace the gas in the gap of the catalyst.

The regenerated catalyst will return to the radial moving bed reactor 1 through the catalyst delivery conduit between the regenerated catalyst receiver 6 and the radial moving bed reactor 1, and continue to participate in the reaction until it is deactivated and delivered to the spent catalyst receiver 5. The catalyst is circulated according to the above protocol. The second particle flow regulator 33 is provided on the communication pipeline of the catalyst outlet of the regenerated catalyst receiver 6 and the catalyst inlet of the radial moving bed reactor 1 to adjust the flow of catalyst particles. Preferably, the first particle flow regulator 25 and the second particle flow regulator 33 are each independently L-shaped or approximately L-shaped stream delivery valve manifold.

On the pipeline starting from the catalyst discharging outlet of the moving bed reactor 1 and the pipeline for discharging the regenerated catalyst from the regenerated catalyst receiver 6 are arranged the catalyst particles lifting liquor pipelines 26, 27 respectively to assist the delivery of the catalyst. On the pipelines for connecting the moving bed reactor 1, the spent catalyst receiver 5, the catalyst regenerator 4, and the regenerated catalyst receiver 6 are arranged the between-vessels stream pipeline valves 28, 34, 35, 36.

The catalyst regenerator is further provided with a fresh catalyst charging inlet 9.

Concerning FIG. 1, the solid acid alkylation process provided by the present invention is illustrated.

Figure 2:
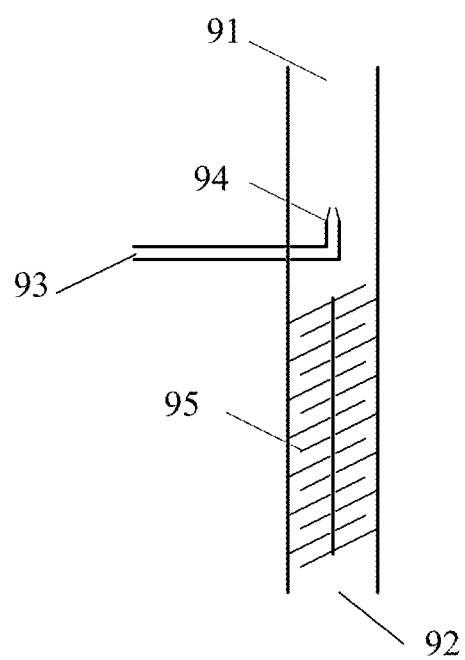
FIG. 2 is a schematic diagram for the structure of the component-based mixer.

An isobutane-containing fresh alkene feedstock is introduced from the fresh feedstock feeding pipe 17 into the component-based mixers 37 before three (namely upper, middle and lower) reaction beds of the radial moving bed reactor 1 respectively through the first branch pipeline 19, the second branch pipeline 20, and the third branch pipeline 21, mixed with the stream in the recycled stream pipe 18 or the stream-after-the-reaction withdrawing pipe 13 from the upstream reaction bed, and then introduced into the reaction stream space 2 through the reaction stream feeding pipe of each reaction bed; the above liquid-phase mixed stream enters the reaction stream distribution zone 12 through the reaction stream space 2, then radially passes through the catalyst bed 3 and contacts with the catalyst to perform the reaction, finally enters the stream-after-the-reaction collection zone 11 and passes through the stream-after-the-reaction withdrawing pipe 13 located thereafter to leave this reaction bed. The discharged stream-after-the-reaction is mixed with the fresh feedstock by the component-based mixer 37 and then sent into the next reaction bed to continue to participate in the reaction, or is discharged off the reactor through the liquid-phase product outlet 22 and distilled to collect the alkylation oil product. the catalyst in every reaction beds of the radial moving bed reactor gradually deactivates along with the reaction, and meanwhile the catalyst gradually falls to the lower reaction bed (optionally via the catalyst bed bottom distribution zone 15), and finally reaches the bottom catalyst-collecting area 14; the catalyst is delivered from the catalyst discharging outlet 23 to the spent catalyst receiver 5, in which the liquid-phase mixed stream carried in the catalyst is removed, and subsequently flows into the catalyst regenerator 4 through the catalyst delivery pipeline 34 at the bottom of the spent catalyst receiver 5; in the catalyst regenerator 4, the catalyst is subjected to the high temperature oxidation regeneration under the oxygen-containing atmosphere or the regeneration under the hydrogen-containing atmosphere to recover its activity; The regenerated catalyst flows into the regenerated catalyst receiver 6 through the catalyst delivery pipeline 35 at the bottom of the catalyst regenerator 4, and the liquid-phase mixed stream is introduced thereto to replace the gas in the gap of the catalyst, and then the regenerated catalyst returns to the radial moving bed reactor 1 via the catalyst delivery pipeline 36 at the bottom of the regenerated catalyst receiver 6 to participate in the reaction until the catalyst is deactivated and then delivered to the spent catalyst receiver 5, and the process is circulated in this manner FIG. 2 is a schematic diagram of the structure of the component-based mixer. As shown in FIG. 2, the component-based mixer in the reaction stream feeding pipeline of the present invention consists of an upper recycled stream pipe 91, a lower feeding pipe 92, and a middle fresh feedstock feeding pipe 93 extending into the reaction stream feeding pipeline, a nozzle 94 of the feeding pipe is arranged at the outlet of the fresh feedstock feeding pipe, a filler and/or a mixing fin 95 is arranged in the reaction stream feeding pipeline.

Figure 3:
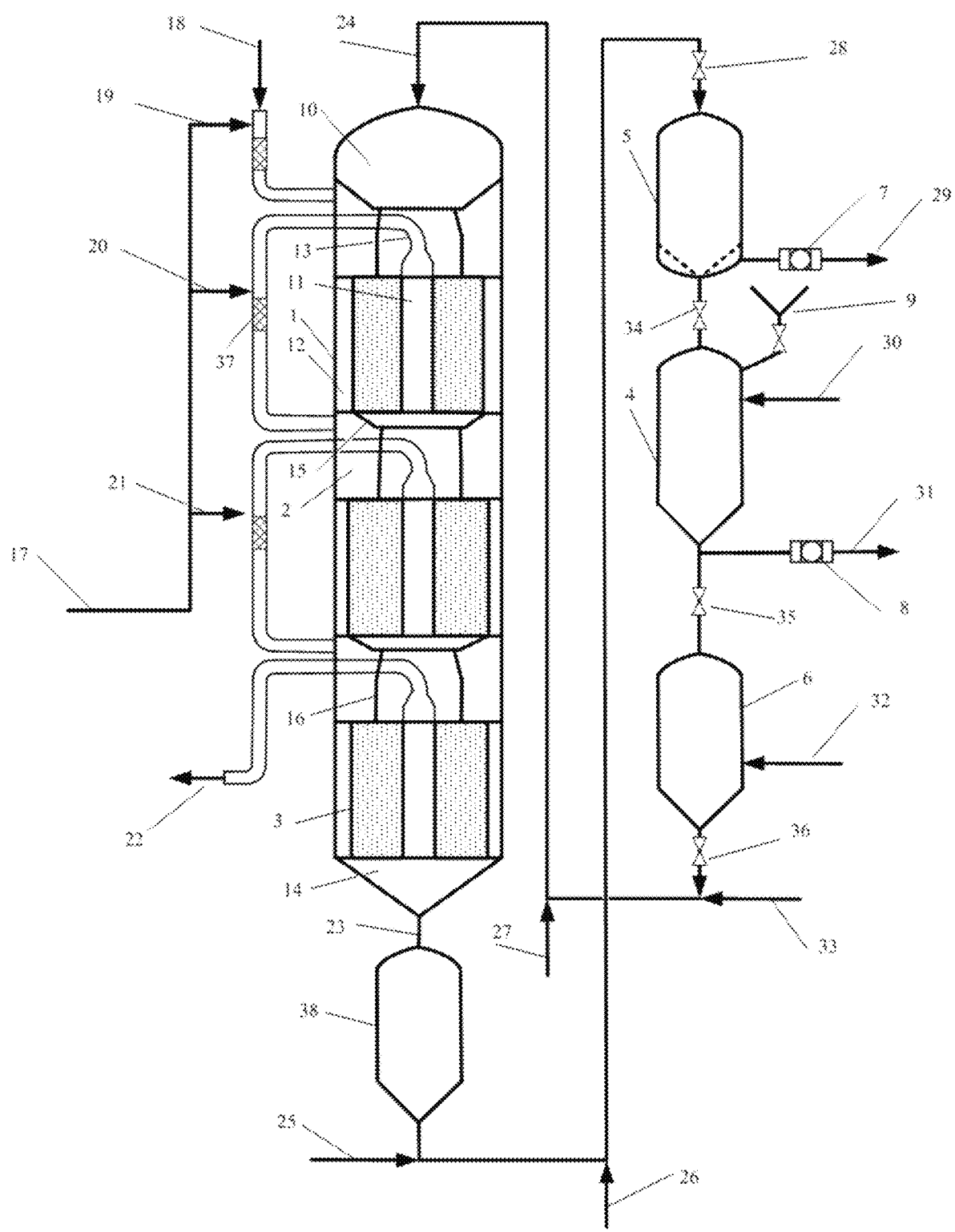
FIG. 3 is a schematic diagram of another embodiment of the radial moving bed reaction apparatus provided by the present invention.

FIG. 3 is a schematic diagram of another embodiment of the radial moving bed reaction apparatus provided by the present invention. The difference from FIG. 1 is that a spent catalyst buffer tank 38 is arranged below the liquid-solid radial moving bed reactor to store the catalyst discharged from the reactor during the periods of withdrawing the liquid-phase mixed stream from the spent catalyst receiver and discharging the catalyst to the catalyst regenerator, and ensure the flow continuity of the catalyst stream in the reactor and the smoothness of the apparatus operation.

Figure 4:
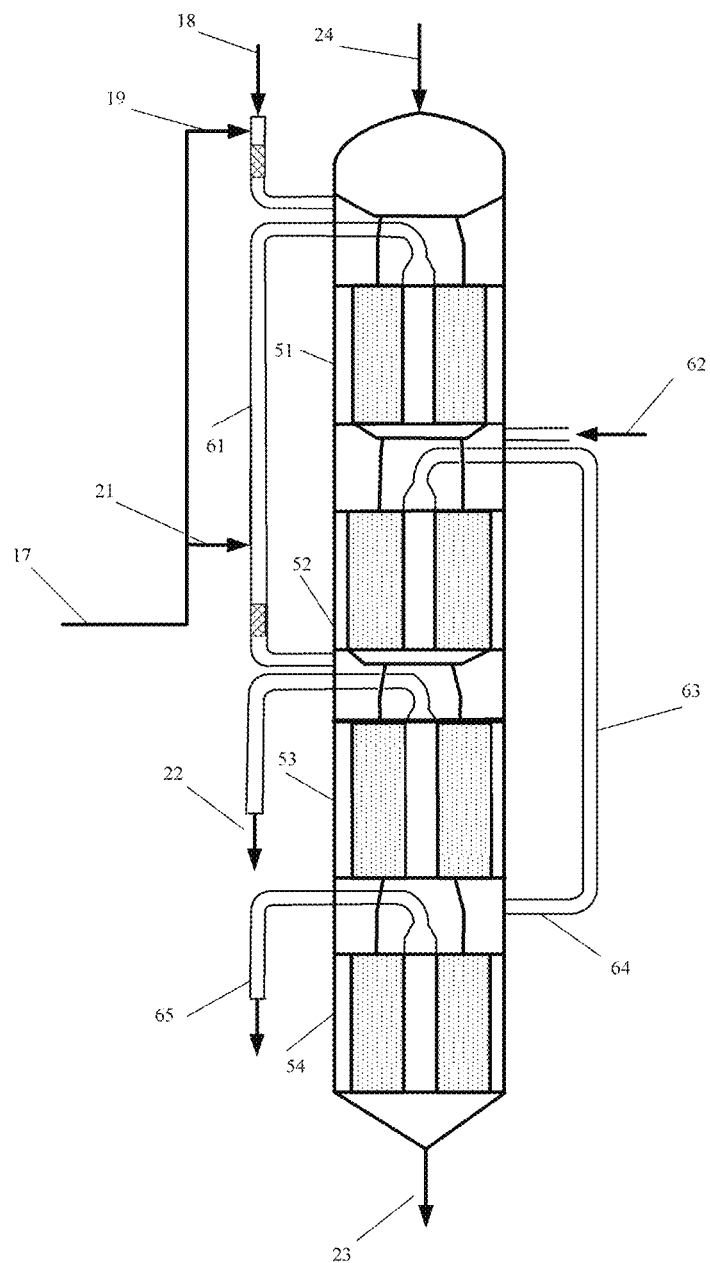
FIG. 4 is a schematic diagram of another embodiment of the radial moving bed reaction apparatus provided by the present invention.

FIG. 4 is a schematic diagram of another embodiment of the radial moving bed reaction apparatus provided by the present invention. The difference from FIG. 1 is that in the radial moving bed reactor are comprised the catalyst reaction beds 51, 53 and the catalyst regeneration beds 52, 54 that are intervally successively arranged;

Each reaction bed comprises a reaction stream distribution zone, a catalyst bed, and a stream-after-the-reaction collection zone, and each reaction bed has a reaction stream feeding pipeline and a stream-after-the-reaction withdrawing pipe, the reaction stream distribution zone is communicated through the reaction stream space with the reaction stream feeding pipeline, the stream-after-the-reaction collection zone is communicated with the stream-after-the-reaction withdrawing pipe, the component-based mixer is arranged on the reaction stream feeding pipeline of each reaction bed;

The regeneration bed has a similar physical structure to the reaction bed, namely, each regeneration bed correspondingly comprises a regeneration medium distribution zone, a catalyst bed, and a regeneration medium collection zone, and each regeneration bed has a regeneration medium feeding pipe and a regeneration medium withdrawing pipe, the regeneration medium distribution zone is communicated via the regeneration medium space with the regeneration medium feeding pipe, the regeneration medium collection zone is communicated with the regeneration medium withdrawing pipe;

Any two adjacent beds of the reaction bed(s) and the regeneration bed(s) are communicated through the catalyst delivery pipe; the catalyst in the reaction bed and the catalyst in the regeneration bed fall through the catalyst delivery pipe from the upstream bed to the adjacent downstream bed, finally, fall to the bottom catalyst-collecting area, and leave the radial moving bed reactor; Preferably, the regeneration medium feeding pipe of any regeneration bed except the first regeneration bed can be or be communicated with the regeneration medium withdrawing pipe of the previous regeneration bed (upstream bed).

With reference to FIG. 4, a process for the solid acid alkylation reaction and regeneration in the presence of hydrogen provided by the present invention is illustrated, wherein a liquid-state fresh feedstock 17,19,21 is mixed with a recycled liquid-phase mixed stream 18 or a stream-after-the-reaction 61 from the upstream reactor and then sent into the reaction bed 51,53 of the radial moving bed reactor; In the reaction bed of the reactor, the mixed stream passes through the reaction bed along the radial direction of the reactor, and contacts with the solid acid catalyst to perform the reaction, after the completion of the reaction, the majority of (for example, >50 vol %, >60 vol %, >70 vol %, >80 vol %, >90 vol %, >95 vol %, >96 vol %, >97 vol %, >98 vol %, or >99 vol %) liquid-phase mixed stream is discharged off this bed through the arranged reaction product discharging outlet, while the minority of the remaining liquid-phase mixed stream, together with the catalyst particles, enters the catalyst regeneration bed 52,54 through the catalyst delivery pipe between the reaction bed and the catalyst regeneration bed; The discharged liquid-phase mixed stream-after-the-reaction 61, is mixed with the fresh feedstock and then sent into the downstream reaction bed of the reactor to to continue to participate in the reaction, or is discharged off the reactor 22, an alkylation oil product is collected by separation (for example distillation). In the catalyst regeneration bed, the fresh regenerating medium 62 enters the catalyst regeneration bed 52 of the radial moving bed reactor through the regenerating medium space and the regenerating medium distribution zone, the unsaturated hydrocarbons adsorbed on the catalyst are converted with the catalyst by contacting with the liquid-phase regeneration medium in which hydrogen is dissolved under the low-temperature regeneration condition to the saturated hydrocarbon molecules that are easily desorbed, and the saturated hydrocarbon molecules are taken out of the regenerator to realize the partial regeneration of the catalyst; the regeneration medium enters the next catalyst regeneration bed via the pipeline 63 that is used as both the regeneration medium withdrawing pipe and the regeneration medium feeding pipe 64 to perform the low-temperature regeneration. The regenerated catalyst flows into the next reaction bed 53 through the catalyst delivery pipe at the bottom of the catalyst regeneration bed; the inactivation degree of the catalyst in every reaction beds and every catalyst regeneration beds of the radial moving bed reactor will gradually increase along with the reaction and the increased regeneration number, and meanwhile, the catalyst will also gradually fall to the lower reaction bed or the lower catalyst regeneration bed, and finally reach the catalyst discharging outlet 23 at the bottom of the radial moving bed reactor; finally, the catalyst is sent to the catalyst regenerator (namely, the high-temperature deep regeneration system) to realize the complete recovery of the catalyst activity; the catalyst with the recovered activity is sent to the catalyst inlet 24 at the top of the radial moving bed reactor to continue to participate in the reaction; the process is circulated in this manner.

According to the process for the solid acid alkylation reaction and regeneration in the presence of hydrogen of the present invention, in the radial moving bed reactor, in the reaction bed, the reaction temperature is 30-100° C., the reaction pressure is 1.0-5.0 MPa, the superficial flow velocity of the liquid-phase mixed stream in the reactor is 0.03-1 m/s; the weight hourly space velocity of the mixed alkene feedstock is 0.05-1 $h^{-1}$; the mole ratio of alkane to alkene at the reaction bed inlet is 200-1000:1; the average particle diameter of the solid acid catalyst particles is 0.3-3 mm;

In the catalyst regeneration bed, the regeneration temperature is 50-140° C., the superficial flow velocity of the regeneration medium in the regeneration bed is 0.01-0.5 m/s;

The main active component of the catalyst is a molecular sieve loaded with a certain amount of metal, said molecular sieve is one of or a combination of two or more of FAU structure zeolite, BETA structure zeolite, and MFI structure zeolite, preferably a zeolite having FAU structure and a zeolite having BETA structure; the metal loaded on the catalyst is one of or a combination of two or more of Fe, Co, Ni, Pd and/or Pt, preferably one of or a combination of two or more of Co, Ni or Pt, more preferably Pt;

The regeneration medium is a liquid hydrocarbon in which hydrogen is dissolved; the liquid hydrocarbon is C3-C5 saturated alkane or a mixture of the reaction product and the above-mentioned saturated alkane, preferably, the liquid hydrocarbon is a mixture of C3-C5 saturated alkane and the reaction product;

In the catalyst regenerator (namely, the high-temperature deep regeneration system), the regeneration temperature is 180-400° C., the regeneration pressure is 0.5-4.0 MPa, the regeneration medium is hydrogen gas or a mixture of hydrogen gas and low carbon hydrocarbon (for example C3-C8), preferably a mixture of hydrogen gas and low carbon hydrocarbon (for example C3-C8). The following examples illustrate the structure and the effect of the liquid-solid moving bed reaction apparatus provided by the present invention. However, the present invention is not limited in any way.

In the following examples and comparative examples:

The used catalyst was an FAU structure molecular sieve spherical catalyst with an average particle size of 1.8 mm. The preparation process thereof was as follows: an FAU structure NaY-type molecular sieve (produced by Sinopec Catalyst Company) was subjected to the ion exchange and the like to remove the sodium ion from the molecular sieve; then the molecular sieve was mixed uniformly with alumina in the weight ratio of 65:35; the pellets were prepared via oil-ammonia column forming method and further dried and calcined to give the catalyst. In the preparation of the catalyst, 0.4% of Pt was also impregnated. The catalyst was put into the reactor after high-temperature air oxidation and high-temperature hydrogen reduction.

The composition and the octane number of the alkylation oil were determined by gas chromatography.

Example 1

The solid acid alkylation reaction was carried out with the liquid-solid radial moving bed reaction apparatus as shown in FIG. 1. Among others, the radial moving bed reactor 1 had a shell inner diameter of 600 mm and included three reaction beds from top to bottom, and each reaction bed had a height of 3.5 m.

The spent catalyst receiver, the catalyst regenerator, and the regenerated catalyst receiver each had a diameter of 1000 mm and a straight-tube segment height of 6 m. The recycled stream pipe or the upstream reaction zone discharging pipeline had a diameter of 250 mm Each reaction zone feeding pipe was provided with a component-based mixer as shown in FIG. 2. For the component-based mixer, the fresh feedstock feeding pipe had an inner diameter of 25 mm, the recycled stream pipe had an inner diameter of 250 mm, and the lower reaction stream feeding pipe had an inner diameter of 250 mm, wherein a nozzle was provided at the outlet of the fresh feedstock feeding pipe.

The alkylation raw material was a mixture of isobutane, n-butane, butene, and the like, and it was introduced from the fresh feedstock feeding pipe 17, and then divided into three ways, each of which was mixed by the component-based mixer and entered the corresponding catalyst bed.

After mixing, the stream had an alkane/alkene mole ratio of 700:1 (namely the alkane/alkene ratio at the reaction bed inlet), the flow velocity in the recycled stream pipe of the reactor was 1.9 m/s, the total feeding rate of the corresponding fresh alkylation raw material was 482 kg/h, and the weight hourly space velocity of the mixed alkene feedstock was 0.25 $h^{-1}$. The reaction temperature was 70° C., and the reaction pressure was 2.5 MPa.

Nitrogen and air (1:1) were used as the high-temperature deep regeneration medium of the catalyst. The periodic time of the high-temperature deep regeneration was 24 hours. Each time, the amount of the catalyst sent to the high-temperature deep regeneration comprised 120 wt % of the total catalyst in the reactor. To guarantee the constant catalyst amount in the reactor, it was necessary to keep the weight of the catalyst being discharged from the reactor was identical to that being supplemented to the reactor through the spent catalyst receiver and the regenerated catalyst receiver. For the regeneration operation, the maximum temperature was 480° C., the pressure was about normal pressure, the superficial gas velocity of nitrogen gas and air as the regeneration medium in the deep regenerator was 0.1 m/s.

After the continuous stable operation of the test apparatus for 1000 hours, the obtained alkylation oil was detected and assessed. The test results were shown in Table 1.

Example 2

The solid acid alkylation reaction was performed with the fluidized bed experimental apparatus as shown in FIG. 3. The solid acid alkylation reaction was performed on a radial moving bed reaction apparatus similar to that of Example 1 except that helical fillers having left and right helical slices that were alternatively arranged were used as the component-based mixers provided on the feeding pipes to the reaction zones.

After the continuous stable operation of the test apparatus for 1000 hours, the obtained alkylation oil was detected and assessed. The test results were shown in Table 1.

Comparative Example 1

The solid acid alkylation reaction was carried out on a medium-sized test apparatus containing two fixed beds connected in parallel. The specific operation process was as follows: when the first reactor was in the alkylation reaction, the second reactor carried out the high-temperature deep regeneration operation, and the two fixed bed reactors connected in parallel were switched for use so that the apparatus could be continuously and stably operated. Each fixed bed reactor had an inner diameter of 200 mm and a height of 2500 mm. The preparation process of the catalyst filled in the reactor was the same as that in Example 1, except that the diameter of the pellet was 2.7 mm, the filling amount was 28 kg, and the filling height was 1500 mm. The reaction feedstock was the same as in Example 1, the molar ratio of alkane to alkene at the reaction bed inlet was 800:1, the feed rate of the fresh mixed alkenes was 6.3 kg/h, and the weight hourly space velocity was 0.09 $h^{-1}$ relative to the alkene. The catalyst in the bed needed a high-temperature deep regeneration once every 24 hours. With the mixed gas of nitrogen and air (identical to Example 1), the catalyst in the bed was subjected to an oxidation regeneration for 3 hours under normal pressure at the reaction temperature from normal temperature to 480° C.; the bed needed to be cooled after the regeneration; the whole regeneration period was 24 hours. After the regeneration was finished, the streams in the reactor in the reaction state were returned to the reactor in which the catalyst had been regenerated, the alkylation reaction experiment was continued with the regenerated catalyst, and the reactor in which the reaction streams had been evacuated was switched to the regeneration operation, the process was circulated in this manner.

After the continuous stable operation of the test apparatus for 1000 hours, the obtained alkylation oil was detected and assessed. The test results were shown in Table 1.

Example 3

This example was carried out in the liquid-solid radial moving bed reactor as shown in FIG. 4, wherein the used spent catalyst receiver, the used catalyst regenerator, and the used regenerated catalyst receiver and other equipment not mentioned herein were identical or similar to those in Example 1.

The radial moving bed reactor had a shell inner diameter of 600 mm and included two reaction beds and two catalyst regeneration beds that were intervally successively arranged, each bed had a height of 3.5 m.

The fresh feedstock for the reaction was identical to that used in Example 1. After feeding through the fresh feedstock feeding pipeline, the feedstock was divided into two ways and mixed with the recycled stream or the liquid-phase mixed stream after the upstream reaction and then each entered the corresponding reaction bed.

After mixing, the molar ratio of alkanes to alkenes of the stream in the distribution zone of the reactor was 700±100:1 (namely, the alkane/alkene ratio at the reaction bed inlet), and the weight hourly space velocity of the mixed alkene feedstock was 0.25 $h^{-1}$.

The same catalyst as in Example 1 was used.

The reaction temperature in the reaction bed was 70° C., and the reaction pressure was 2.5 MPa.

In the catalyst regeneration bed, the liquid-phase mixed stream after the reaction, containing a part of alkylation oils and in which hydrogen is dissolved, was used as the regeneration medium of the catalyst. The regeneration conditions such as temperature and pressure were similar to the reaction conditions such as temperature and pressure.

The total residence time of the catalyst in the radial moving bed reactor was controlled to 168*h*.

The catalyst that finally lost its activity was introduced into the high-temperature deep regeneration system. The deep regeneration was performed at the regeneration temperature of 280° C. and the regeneration pressure of 2.5 MPa with hydrogen gas containing some low-carbon hydrocarbons to completely restore the catalyst activity.

After the activity was restored, the catalyst was reintroduced to the fresh catalyst feeding inlet at the top of the reactor to continue to participate in the reaction, and the process is circulated in this manner.

After the continuous stable operation of the test apparatus for 1000 hours, the obtained alkylation oil was detected and assessed. The test results were shown in Table 1.

TABLE 1

Operation results of the apparatus in the examples and property comparison of alkylation products

| Embodiment | RON | MON | Alkene C5+ yield | TMP/DMH | C9+ Product wt % | Catalyst residence time |
|---|---|---|---|---|---|---|
| Example 1 | 95.5 | 91.5 | 1.99 | 3.53 | 5.12 | 24 h |
| Example 2 | 95.7 | 91.7 | 2.0 | 3.62 | 5.10 | 24 h |
| Example 3 | 95.6 | 92.0 | 1.94 | 3.67 | 5.32 | 168 h |
| Comparative Example 1 | 95.2 | 91.3 | 1.96 | 3.24 | 6.76 | 24 h |

As can be seen from Table 1, the octane number of the alkylation oil obtained by adopting the liquid-solid radial moving bed reaction apparatus provided by the present invention to the solid acid alkylation reaction was slightly better than that of the fixed bed technology, the alkene yield in the alkylation oil was higher, the target product (trimethylpentane) selectivity was higher, and the yield of the C9+ product was lower. Better product yield and target product selectivity were obtained. From the view of the apparatus operation, for the fixed bed alkylation technology, in order to realize the continuous and stable operation of the reaction apparatus, at least two or more reactors were required to be switched. The catalyst in the bed was subjected to high-temperature oxidation regeneration at regular intervals, and it was necessary to cool the high-temperature bed after the deep regeneration. Since the apparatus was frequently switched between 70° C. and 480° C., a plurality of problems were caused in the continuous and stable operation in industrial applications. But the radial moving bed technology provided by the invention can meet the requirements with a single (set of) equipment. The investment cost of the apparatus was reduced. In addition, the inactivated catalyst particles were led out of the reactor to carry out the deep regeneration, under the premise of not influencing the stable operation of the reaction apparatus, the continuous operation of the reaction with catalyst and the catalyst regeneration was realized, the stable equilibrium activity of the catalyst in the apparatus was maintained, the selectivity of the target product in the alkylation oil was improved.

The invention claimed is:

1. A liquid-solid radial moving bed reaction apparatus, wherein the apparatus comprises:
   a radial moving bed reactor, a spent catalyst receiver, a catalyst regenerator, and a regenerated catalyst receiver that are successively connected, wherein a catalyst discharging outlet of the regenerated catalyst receiver is communicated with a catalyst inlet of the radial moving bed reactor;
   characterized in that:
   the radial moving bed reactor is provided with at least two reaction beds and at least one regeneration bed, the at least two reaction beds and the at least one regeneration bed are arranged up and down in the radial moving bed reactor;
   each reaction bed comprises a reaction stream distribution zone, a catalyst bed of the reaction bed, and a stream-after-the-reaction collection zone that are arranged in the radial moving bed reactor such that a reaction stream flows radially inward from the reaction stream distribution zone to the stream-after-the-reaction collection zone or flows radially outward from the reaction stream distribution zone to the stream-after-the-reaction collection zone, and
   each reaction bed has a reaction stream feeding pipeline and a stream-after-the-reaction withdrawing pipe,
   reaction stream spaces are arranged between two reaction beds and between a first reaction bed and a top catalyst collection zone,
   each reaction stream distribution zone is communicated through the corresponding reaction stream space with the corresponding reaction stream feeding pipeline; and a component-based mixer is arranged on the corresponding reaction stream feeding pipeline of each corresponding reaction bed;
   the stream-after-the-reaction collection zone for a reaction bed is communicated with the stream-after-the-reaction withdrawing pipe for the corresponding reaction bed;
   wherein the component-based mixer consists of a recycled stream pipe at an upper part, a reaction stream feeding pipe at a lower part, and a fresh feedstock feeding pipe extending into the reaction stream feeding pipeline, a nozzle of the fresh feedstock feeding pipe is arranged at an outlet of the fresh feedstock feeding pipe, a filler and/or a mixing fin is arranged in the reaction stream feeding pipeline, wherein the component-based mixer is located outside the radial moving bed reactor;
   each regeneration bed comprises a regeneration medium distribution zone, a catalyst bed of the regeneration bed, and a regeneration medium collection zone, and each regeneration bed has a regeneration medium feeding pipe and a regeneration medium withdrawing pipe, wherein the regeneration medium distribution zone is communicated via a regeneration medium space with the regeneration medium feeding pipe, and the regeneration medium collection zone is communicated with the regeneration medium withdrawing pipe; and
   any two adjacent beds of the at least two reaction beds and the at least one regeneration bed are communicated through a catalyst delivery pipe so that a catalyst can move in the radial moving bed reactor from top to bottom; the catalyst in the at least two reaction beds and the catalyst in the at least one regeneration bed fall through the catalyst delivery pipe from a previous bed to a next bed, finally, fall to a bottom catalyst-collecting area, and leave the radial moving bed reactor.

2. The liquid-solid radial moving bed reaction apparatus according to claim 1, wherein an L-shaped or approximately L-shaped stream delivery valve manifold is arranged on a pipeline between a catalyst discharging outlet at a bottom of the radial moving bed reactor and the spent catalyst receiver, and the discharge rate of the catalyst is regulated by changing the flow of a liquid-phase mixed stream into the valve manifold.

3. The liquid-solid radial moving bed reaction apparatus according to claim 1, wherein the top catalyst collection zone is arranged at a top part of the radial moving bed reactor, and a catalyst inlet is communicated through the top catalyst collection zone with a catalyst delivery pipe.

4. The liquid-solid radial moving bed reaction apparatus according to claim 1, wherein in the radial moving bed reactor, the recycled stream pipe of the component-based mixer of a next reaction bed is the stream-after-the-reaction withdrawing pipe of a previous reaction bed or is communicated with the stream-after-the-reaction withdrawing pipe of a previous reaction bed.

5. The liquid-solid radial moving bed reaction apparatus according to claim 1, wherein catalyst circulation pipelines for connecting the spent catalyst receiver, the catalyst regenerator, and the regenerated catalyst receiver are arranged vertically or inclined at an angle relative to the horizontal plane of not less than 40 degrees.

6. The liquid-solid radial moving bed reaction apparatus according to claim 1, wherein the catalyst regenerator or the regenerated catalyst receiver is further provided with a fresh catalyst charging inlet.

7. The liquid-solid radial moving bed reaction apparatus according to claim 1, wherein
the catalyst regenerator comprises a straight-tube segment and a bottom discharging pipeline,
a regeneration medium inlet is arranged at an upper part of the catalyst regenerator, a regeneration medium outlet is arranged at a lower part of the straight-tube segment of the catalyst regenerator or arranged at the bottom discharging pipeline; wherein the regeneration medium inlet is positioned at 70% or higher of the straight-tube segment of the catalyst regenerator from bottom to top, and the regeneration medium outlet is positioned at 20% or lower of the straight-tube segment of the catalyst regenerator from bottom to top.

8. The liquid-solid radial moving bed reaction apparatus according to claim 7, wherein a pipeline starting from the regeneration medium outlet of the catalyst regenerator is further provided with a filter.

9. The liquid-solid radial moving bed reaction apparatus according to claim 1, wherein
the spent catalyst receiver comprises a bottom discharging pipeline; and
a liquid-phase mixed stream discharging outlet is arranged at a bottom of the spent catalyst receiver or arranged at the bottom discharging pipeline of the spent catalyst receiver.

10. The liquid-solid radial moving bed reaction apparatus according to claim 1, wherein in each component-based mixer, the ratio of the cross-sectional area of the fresh feedstock feeding pipe to the cross-sectional area of the recycled stream pipe is in a range of 0.001-0.5:1.

11. The liquid-solid radial moving bed reaction apparatus according to claim 10, wherein in each component-based mixer, the ratio of the cross-sectional area of the fresh feedstock feeding pipe to the cross-sectional area of the recycled stream pipe is in a range of 0.002-0.1:1.

12. The liquid-solid radial moving bed reaction apparatus according to claim 1, wherein the number of the at least two reaction beds is 2-8, and the number of the at least one regeneration bed is 2-8.

13. The liquid-solid radial moving bed reaction apparatus according to claim 12, wherein the number of the regeneration beds is 2-7.

14. The liquid-solid radial moving bed reaction apparatus according to claim 12, wherein the number of the regeneration beds and the number of the reaction beds are identical, and each regeneration bed is arranged immediately under each reaction bed.

15. The liquid-solid radial moving bed reaction apparatus according to claim 12, wherein the number of the regeneration beds is one less than the number of the reaction beds, the reaction beds and the regeneration beds are intervally successively arranged, and two reaction beds are arranged at the top part and at a bottom of the radial moving bed reactor, respectively.

16. The liquid-solid radial moving bed reaction apparatus according to claim 12, wherein the regeneration medium feeding pipe of each regeneration bed except a first regeneration bed is the regeneration medium withdrawing pipe of a previous regeneration bed, or is communicated with the regeneration medium withdrawing pipe of the previous regeneration bed.

17. A solid acid alkylation process, comprising using the liquid-solid radial moving bed reaction apparatus according to claim 1 to perform the following steps:
for each reaction bed, mixing an alkylation raw material and a recycled stream with the component-based mixer and sending the formed mixture to the radial moving bed reactor as a liquid-phase mixed stream; distributing the liquid-phase mixed stream in the reaction stream distribution zone, and passing the liquid-phase mixed stream through the catalyst bed along the radial direction to contact with a solid acid catalyst to produce a liquid-phase mixed stream-after-the-reaction;
for each reaction bed, sending the liquid-phase mixed stream-after-the-reaction to the stream-after-the-reaction collection zone to be used as the recycled stream or further separated to produce an alkylation oil product;
the solid acid catalyst in the catalyst beds of the reaction beds and the at least one regeneration bed of the radial moving bed, falling bed by bed, and finally falling to the bottom catalyst-collecting area, and leaving the radial moving bed reactor to enter into the spent catalyst receiver;
removing the liquid-phase mixed stream carried in the catalyst in the spent catalyst receiver to obtain a spent catalyst;
sending the spent catalyst into the catalyst regenerator to perform a regeneration reaction to obtain a regenerated catalyst with recovered activity;
sending the regenerated catalyst into the regenerated catalyst receiver, and obtaining a regenerated catalyst to be recycled after replacing and removing gas in the regenerated catalyst receiver, and
returning the regenerated catalyst to be recycled to the radial moving bed reactor for continuous reaction.

18. The solid acid alkylation process according to claim 17, wherein the alkylation raw material is a hydrocarbon fraction comprising alkenes and alkanes.

19. The solid acid alkylation process according to claim 18, wherein in the radial moving bed reactor, the reaction temperature is in a range of 30-100° C., the superficial flow velocity of the liquid-phase mixed stream in the radial moving bed reactor is in a range of 0.05-1 m/s; the weight hourly space velocity of the alkylation raw material, based on alkene, is in a range of 0.05-1 $h^{-1}$; a mole ratio of alkane to alkene at an inlet of the radial moving bed reactor is in a range of 200-1000:1; and the solid acid catalyst has an average particle diameter in a range of 0.3-3 mm.

20. The solid acid alkylation process according to claim 17, wherein the solid acid catalyst comprises 95 wt %-65 wt % of a molecular sieve and 5 wt %-35 wt % of a heat-resistant inorganic oxide, wherein the molecular sieve is one or more selected from FAU structure zeolite, BETA structure zeolite, and MFI structure zeolite, and the heat-resistant inorganic oxide is alumina and/or silica.

21. The solid acid alkylation process according to claim 17, wherein in the catalyst regenerator, the spent catalyst and an oxygen-containing gas are subjected to the regeneration reaction, which is an oxidizing reaction under the conditions of the temperature in a range of 200-500° C. and the pressure in a range of 0.01-0.5 MPa, and carbon deposited on the spent catalyst is removed to recover the activity of the catalyst.

22. The solid acid alkylation process according to claim 17, wherein in the catalyst regenerator, the spent catalyst is contacted with a hydrogen gas-containing regeneration medium to perform the regeneration reaction, carbon deposited on the spent catalyst is removed to recover the activity of the catalyst, the regeneration temperature is in a range of 100-400° C., and the regeneration pressure is in a range of 0.5-3.5 MPa.

23. A solid acid alkylation process, comprising using the liquid-solid radial moving bed reaction apparatus according to claim 1 to perform the following steps:
  mixing a fresh feedstock and a recycled stream or a stream-after-the-reaction from a previous reaction bed and then sending the resulting mixed stream into the reaction beds of the radial moving bed reactor;
  in each reaction bed of the radial moving bed reactor, passing the mixed stream through the corresponding reaction bed along the radial direction of the radial moving bed reactor to contact with a solid acid catalyst in form of catalyst particles to perform an alkylation reaction,
  wherein the fresh feedstock is a hydrocarbon fraction comprising alkenes and alkanes,
  after the completion of the alkylation reaction, discharging a majority of the resulting liquid-phase mixed stream off the corresponding reaction bed through a reaction product discharging outlet, while sending a minority of the remaining liquid-phase mixed stream, together with the catalyst particles, into a next reaction bed through a catalyst delivery pipe or into a next catalyst regeneration bed through a catalyst delivery pipe between the current reaction bed and the next catalyst regeneration bed;
  mixing the discharged liquid-phase mixed stream-after-the-reaction with the fresh feedstock and then sending the formed mixture into said next reaction bed to continue to participate in the reaction, or discharging the discharged liquid-phase mixed stream-after-the-reaction off the reactor, and collecting an alkylation oil product by separation;
  in a catalyst regeneration bed, sending a regenerating medium into the catalyst regeneration bed of the radial moving bed reactor through the regenerating medium space and the regenerating medium distribution zone, converting unsaturated hydrocarbons adsorbed on the catalyst with the catalyst by contacting with a liquid-phase regeneration medium in which hydrogen is dissolved under a low-temperature regeneration condition to form saturated hydrocarbon molecules that are easily desorbed, and taking the saturated hydrocarbon molecules out of the regenerator to realize partial regeneration of the catalyst;
  optionally sending the regeneration medium into a next catalyst regeneration bed via a pipeline to perform a low-temperature regeneration;
  a low-temperature regenerated catalyst flows into a next reaction bed through the catalyst delivery pipe at a bottom of the catalyst regeneration bed;
  the inactivation degree of the catalyst in every reaction bed and every catalyst regeneration bed of the radial moving bed reactor gradually increases along with the reaction and an increased regeneration cycle number, and meanwhile, the catalyst also gradually falls to a lower reaction bed or a lower catalyst regeneration bed, and finally reaches a catalyst discharging outlet at a bottom of the radial moving bed reactor; finally, the catalyst is sent to the catalyst regenerator to perform a high-temperature deep regeneration to realize the complete recovery of the catalyst activity;
  the catalyst with recovered activity is sent to the catalyst inlet at the top part of the radial moving bed reactor to continue to participate in the reaction;
  in the radial moving bed reactor, in each reaction bed, the reaction temperature is in a range of 30-100° C., the reaction pressure is in a range of 1.0-5.0 MPa, the superficial flow velocity of the liquid-phase mixed stream in the reactor is in a range of 0.03-1 m/s; the weight hourly space velocity of the formed mixture of the discharged liquid-phase mixed stream-after-the-reaction and the fresh feedstock, based on alkene, is in a range of 0.05-1 h-1; a mole ratio of alkane to alkene of the formed mixture of the discharged liquid-phase mixed stream-after-the-reaction and the fresh feedstock at an inlet of the reaction bed is in a range of 200-1000:1; the solid acid catalyst has an average particle diameter in a range of 0.3-3 mm;
  in each catalyst regeneration bed, the regeneration temperature is in a range of 50-140° C., the superficial flow velocity of the regeneration medium in each regeneration bed is in a range of 0.01-0.5 m/s; the regeneration medium is a liquid hydrocarbon in which hydrogen is dissolved; the liquid hydrocarbon is C3-C5 saturated alkane or a mixture of the reaction product and the C3-C5 saturated alkane;
  the main active component of the catalyst is a molecular sieve loaded with metal, wherein the molecular sieve is one or more of FAU structure zeolite, BETA structure zeolite, and MFI structure zeolite; and the metal loaded on the catalyst is one or more of Fe, Co, Ni, Pd and Pt; and
  in the catalyst regenerator, the regeneration temperature is in a range of 180-400° C., the regeneration pressure is in a range of 0.5-4.0 MPa, the regeneration medium is hydrogen gas or a mixture of hydrogen gas and low carbon hydrocarbon.

24. The solid acid alkylation process according to claim 23, wherein in each catalyst regeneration bed, the liquid hydrocarbon is a mixture of the reaction product and C3-C5 saturated alkane.

25. The solid acid alkylation process according to claim 23, wherein the molecular sieve is a zeolite having FAU structure and a zeolite having BETA structure.

26. The solid acid alkylation process according to claim 23, wherein the metal loaded on the catalyst is one or more of Co, Ni, and Pt.

27. The solid acid alkylation process according to claim 26, wherein the metal loaded on the catalyst is Pt.

28. The solid acid alkylation process according to claim 23, wherein in the catalyst regenerator, the regeneration medium is a mixture of hydrogen gas and low carbon hydrocarbon.

* * * * *